US005800360A

United States Patent [19]

Kisner et al.

[11] Patent Number: 5,800,360

[45] Date of Patent: Sep. 1, 1998

[54] APPARATUS AND METHOD FOR RESPIRATORY MONITORING

[75] Inventors: Roger A. Kisner; Steven P. Baker, both of Knoxville, Tenn.; R. Bennett Muskin, Madison, Conn.

[73] Assignee: Spectrum Medical Technologies, Inc., Powell, Tenn.

[21] Appl. No.: 474,457

[22] Filed: Jun. 7, 1995

Related U.S. Application Data

[60] Continuation-in-part of Ser. No. 209,664, Mar. 9, 1994, abandoned, which is a division of Ser. No. 833,762, Feb. 11, 1992, Pat. No. 5,309,921.

[51] Int. Cl.$^6$ .......... A61B 5/08

[52] U.S. Cl. .......... 600/532

[58] Field of Search .......... 128/719, 920; 600/532

[56] References Cited

U.S. PATENT DOCUMENTS

| | | | |
|---|---|---|---|
| 3,796,208 | 3/1974 | Bloice . | |
| 4,011,859 | 3/1977 | Frankenberger . | |
| 4,350,166 | 9/1982 | Mobarry . | |
| 4,522,204 | 6/1985 | Kurahashi et al. | 128/719 |
| 4,595,016 | 6/1986 | Fertig et al. . | |
| 4,648,396 | 3/1987 | Raemer . | |
| 4,738,266 | 4/1988 | Thatcher . | |
| 4,800,278 | 1/1989 | Taniguti et al. . | |
| 4,928,703 | 5/1990 | Wong . | |
| 4,947,152 | 8/1990 | Hodges . | |
| 4,955,946 | 9/1990 | Mount et al. . | |
| 4,973,843 | 11/1990 | Murata et al. . | |
| 4,980,566 | 12/1990 | Heilweil . | |
| 5,081,998 | 1/1992 | Yelogerman | 128/719 |
| 5,095,900 | 3/1992 | Fertig et al. | 128/719 |
| 5,124,552 | 6/1992 | Anderson . | |
| 5,179,002 | 1/1993 | Fehder | 128/719 |
| 5,282,473 | 2/1994 | Braig et al. | 128/719 |

FOREIGN PATENT DOCUMENTS

| | | | |
|---|---|---|---|
| 2707090 | 8/1978 | Germany | 128/719 |

*Primary Examiner*—William E. Kamm
*Attorney, Agent, or Firm*—Luedeka, Neely & Graham P.C.

[57] ABSTRACT

A passive, non-invasive, non-contacting apparatus and method for monitoring the respiration of a subject within a monitored environment is disclosed. The apparatus generally comprises a pair of sensors which detect changes in infrared energy. The first sensor detects changes in infrared energy which signifies and corresponds to changes in the monitored environments of a component to be monitored and generates a first signal. The second sensor detects changes in infrared energy which signifies reference infrared energy in the monitored environment and generates a second signal. A processing system converts the first and second signals into a third signal which signifies the concentration of the monitored component in the monitored environment. The monitored components may be $CO_2$ $H_2O$ or a constituent of exhaled breath such as a ketone, amino acid, insulin or pintane. In another embodiment of the invention changes in blood pH may be monitored by adding an additional sensor. Micromotion of the subject's body may also be monitored in yet another embodiment through the use of a single sensor together with an appropriate processing system. Imaging techniques may be employed to accomplish high resolution monitoring of the monitored environment.

43 Claims, 11 Drawing Sheets

APPARATUS AND METHOD FOR RESPIRATORY MONITORING

This is a Continuation in Part of prior application Ser. No. 08/209,664, filed Mar. 9, 1994, now abandoned which is a divisional of application Ser. No. 07/833,762, filed Feb. 11, 1992, which issued as U.S. Pat. No. 5,309,921 on May 10, 1994.

BACKGROUND OF THE INVENTION

In general, a change in an individual's respiration (known as "apnea" when such a change is a transient cessation of respiration) corresponds to a change in the physical condition of that individual. In the case of invalids, infants, the elderly, hospitalized patients, or individuals with obstructive sleep apnea, a change in respiration may be attributable to present or impending physical distress. Accordingly, an urgent need exists for an improved respiratory monitoring system for such individuals that will meet technical and clinical needs for reliable monitoring of individuals at risk of respiratory distress. Many such individuals are in need of such a system, as many are unable to summon help because they may be asleep, handicapped, bedridden, hospitalized or otherwise unable to communicate. There is an especially critical need to continuously monitor some infants from birth through one year. Accordingly, the present invention relates to a pioneering, non-invasive, non-contacting, safe system which monitors the respiratory functions and/or fluctuations in exhaled breath including carbon dioxide ($CO_2$), water vapor, various constituents in the blood gases and which determines other functions and/or fluctuations including the pH level of an individual's blood as well as the motion of the subject.

The presence of $CO_2$ and other component gases present in exhaled breath can be detected by measuring the breath's absorption of specific wavelengths of light. With an increase in concentration of a component gas, comes a decrease in transmission of those specific wavelengths. Thus, if an emitter and a detector of infrared energy in an absorption band of a component gas are separated by an open distance, the presence (and perhaps the concentration) of gas in that open environment can be evaluated. Two basic system types can be constructed that use this principle of illumination to measure absorption characteristics: those that use a powered source of interrogation energy—called active systems; and those that use sources of energy naturally occurring in the environment—called passive systems. The passive system offers a more reliable method for monitoring a patient's respiration. A discussion of both types of systems follows:

A powered emission device and a detector comprise an active detection system. Gases passing between the emitter-detector pair will be detected and measured. Thus, it is important that the geometry of the emitter and detector be arranged to allow for the passage of a patient's breath between them. The distances can be made larger by increasing emission intensity or improving detector sensitivity (or both). The detector can be made receptive to incoming energy over a wide angle of view. Even with a wider view angle, however, only gases between the detector and the emitter will be measured. Thus, multiple emitters are required to achieve a larger detection zone volume.

Patients may assume numerous positions and orientations while being monitored. Therefore, to effect detection of $CO_2$ in breath, when using an active system would require many emitters and detectors placed at various locations within certain proximity to the patient. Theoretically, breath, whether it travels to the side or upwards, could be detected if enough emitters and detectors were placed in enough orientations and angles. Unfortunately, some of the detectors or emitters would need to be under the patient (in the mattress if the patient is being monitored in bed for example) so as to catch breath from a patient in a side-facing position. This may not be possible from a practical point of view. Other problems with the active emitter approach include cost of the large number of emitters and detectors required to form a relative uniform region of detection, the unreliability of such a large number of components, the complicated apparatus that would be required to house such a system, and the complexity of electronics required to control the process data from numerous emitters and detectors.

In addition to the above-stated drawbacks, active emitters require a source of power. Photon emission is inefficient at the wavelengths of interest (i.e., 4 to 20 microns for many carbon-containing molecules). The large amounts of power needed also require a large battery to supply backup power during loss-of-power events. This also may be a substantial drawback.

In a passive system, the patient and surrounding environment become the source of interrogating energy. Thus, all of the problems are eliminated that are associated with employing multiple emitters as discussed above. The requirements then placed on the detector assemblies are that they respond to the wavelengths emitted by the surroundings, are capable of wide-angle coverage, are sensitive enough to detect the depression in infrared energy due to presence of $CO_2$, or other component being detected, regardless of patient orientation. The invention described herein may utilize a reference detector to cancel unwanted variation since the emitter in this system is a highly variable energy source (e.g., temperature and patient motion affect emission). A passive emission infrared gas detection system is superior to an active system in cost, reliability, and performance if these requirements are met.

Presently, devices exist on the market that monitor a patient's respiration. These devices, known as capnographs, monitor the exhaled $CO_2$ from a patient's airways by continuously sampling the exhaled breaths. However, unlike the present invention, capnographs, require a physical attachment between the capnograph and the patient's airways. This attachment limits the clinical applications of the capnograph to intubated patients or short term monitoring applications. And even in these limited applications many difficulties arise in the monitoring process, difficulties such as mucous plugs or other secretions blocking the sampling tube, patient movements disrupting the positioning of the sampling line, agitated patients pulling the sampling tube out of position, etc., all add to inaccuracies in the measurements taken and to the inconvenience of using the device.

Other respiratory monitoring systems have been proposed. For example, a non-contacting apnea detector is disclosed in U.S. Pat. No. 4,350,166 (Mobarry). This device monitors carbon dioxide ($CO_2$) exhaled by an infant by detecting the difference in the infrared ("IR") radiation caused by the absorption of IR energy by exhaled $CO_2$ of the patient. However, this device does not have the capability of accounting for changes in the level of infrared radiation caused by other factors such as the patient's general body movements, repositioning of the patient, or general disruptions in the IR energies emitted from the crib (as could be caused, for example, by a warm nursing bottle).

In U.S. Pat. No. 4,738,266, Thatcher discloses non-contact monitoring device which allegedly contains improvements over the Mobarry system. The Thatcher device contains an infrared radiating element in the system. The detection of the infant's breathing is directly related to whether the requisite amount of carbon dioxide has passed through the device-produced infrared radiation. Changes in the radiation level are registered and compared to the desired value. The infant's exhaled breath must pass through this IR source in a constant manner, or else detector values with be erroneous. This device has great clinical limitations.

Another device, which is allegedly an improvement over the Mobarry system, is disclosed in U.S. Pat. No. 4,928,703 (Wong). Wong mentions the problems associated with passive sources of radiation, such as from the patient's own motions, which are detected by the Mobarry system and which compromise the device's accuracy. The Wong device, like the Thatcher device, includes a means for emitting radiation. The radiation generated is subsequently collected and measured to determine the amount of carbon dioxide in the path of the radiation as it travels between an emitter and a collector. The only signal monitored by the Wong device is that related to the absorbed radiation which corresponds to the infant's exhaled carbon dioxide. However, this device still requires an artificial means for emitting infrared radiation, which inherently limits the number of locations at which the device can be positioned such that it operates safely and effectively. Its battery power requirements in the event of loss or unavailability of a.c. power are also excessive. Accordingly, the need still exists for a safe, reliable non-invasive, non-contacting system for monitoring an individual's respiratory condition which does not require an artificial source of infrared energy, which is capable of differentiating between infrared energy absorbed by a particular component such as carbon dioxide and other forms of infrared energy, and which may be mounted in a variety of locations without sacrificing effectiveness.

SUMMARY OF THE INVENTION

In accordance with this invention, respiratory monitoring of individuals in a variety of settings may be achieved in a non-invasive, non-contacting, comfortable, accurate and safe manner by detecting infrared energy along the entire spectrum, even in the presence of wideband IR interference, without the need for a supplemental or active source of infrared energy. This is accomplished by detecting changes in infrared energy emitted by various sources such as the human body and by converting the detected energy into a form by which others may be alerted to a change in the well-being of the patient.

Humans, being at a core temperature of 98.6° F. and skin temperature above ambient, are radiators of infrared energy over a wide spectral range. The emission of infrared energy is dependent upon body temperature, skin emissivity, shielding materials (e.g., clothing and blankets), movement, and changes in concentrations of certain gases in the path between the human and a detector of infrared energy. In accordance with the invention, the emitted energy of both the patient and his surroundings is used to illuminate detectors, which may be placed in a variety of locations, for example, above the patient or to his side.

Carbon dioxide, a gas constituent of exhaled breath, is an absorber of infrared energy at specific wavelengths. Measurement of infrared energy absorption in the $CO_2$ spectrum indicates variations in the concentration of $CO_2$, which directly corresponds to the process of breathing.

A non-invasive, non-contacting system has been designed and constructed, which employs a plurality of, but no less than two infrared sensors capable of detecting different infrared bandwidths. Each sensor is equipped with a pyroelectric crystal and special optical filter so that a specific range of infrared wavelengths can be admitted. One sensor, the "reference" sensor, responds to changes in infrared energy outside of the wavelengths of a particular component in the area being monitored. The second sensor, the "component" sensor, responds to changes in the range of infrared wavelengths corresponding to the absorption bands of the component to be measured, for example, the absorption bands of $CO_2$ or $H_2O$.

There are three possible variations in the assignment of range and overlap of wavelengths for the two infrared sensors:

(1) The reference sensor responds to changes in infrared energy outside the wavelengths of a particular component in the area or environment to be monitored. The component sensor responds to the specific wavelengths of the component. Thus the reference sensor senses overall deviations in the amount and rate of infrared energy emitted and in the emissivity of the environment while the component sensor senses deviations arising only from changes in the component wavelength range, which may be influenced by the same effects causing deviations in the reference spectrum. No overlap exists between the spectrums of the reference and component sensors.

(2) The reference sensor responds to changes in infrared energy outside the wavelengths of a particular component in the area or environment being monitored. The component sensor responds to the same wavelengths as the reference sensor and, in addition, responds to the wavelengths of the particular component to be measured. For example, in addition to $CO_2$, the sensor may be adapted to sense changes in wavelengths corresponding to the body temperature, skin emissivity, shielding materials, movement, and changes in concentrations of certain gases in the path between the patient and the sensor. In this variation, the component sensor overlaps the reference sensor's spectrum; and (3) The reference sensor responds to changes in a range of wavelengths that spans both the non-component infrared region and a component region. The component sensor responds to the specific wavelengths of the component only. In this variation the reference sensor overlaps the component sensor's spectrum.

Any of the foregoing variations in the assignment of range and overlap of wavelengths for the two infrared sensors may be adapted for use in all of the embodiments of the invention described herein.

Because the presence of infrared energy from various sources from other than the intended source (e.g. body motion, ambient light etc.) in the monitored environment, the component sensor is modulated by general motion of the patient as well as other factors which affect the amount of infrared energy (such as changes in the concentration of the component of interest), a new signal must be derived by converting the reference sensor signal and the component sensor signal into a third signal signifying the concentration of the monitored component from which the infrared energy from other than the component source has been removed. The new signal is a reflection of variations in the component concentration along the optical pathway. In the case of a $CO_2$ component, this signal can be further filtered and digitally processed to enhance the breathing component, which can then be analyzed in real-time to determine the breathing rate and relative intensity. In the case of an $H_2O$ component, this signal can be further filtered and digitally processed to enhance a water vapor component which can then be analyzed in real-time to determine the depth of breathing (i.e. the volume of expired air). Also, an $H_2O$ sensor used in conjunction with a $CO_2$ sensor to produce a signal which corresponds to the ratio of the signals derived from the $H_2O$ and $CO_2$ sensors may further be processed to determine the trends in blood pH levels. Moreover, other constituents of exhaled breath, such as ketones, amino acids, insulin, pintane and the like may be detected in a similar fashion.

Each embodiment of the invention may employ one or more sensors to generate a matrix of signals that represent, in effect, an image of the monitored environment where each pixel of the image is represented by a signal read from a sensor while monitoring a particular area of the monitored environment corresponding to the location of the pixel in the image. Such imaging enables a high degree of resolution in monitoring respiratory components and body motion. Imaging can be accomplished with a single sensor that has an instantaneous field of view that covers the entire monitored environment, or it may be accomplished by the employment of more than one sensor. Optical scanning techniques may be required, depending on the arrangement of the sensors.

Accordingly, it is an object of the present invention to provide a non-contacting, non-invasive apparatus which detects changes in the respiratory condition of an individual by monitoring changes in infrared emissions, without the need for active or supplemental infrared emitter or other supplemental electromagnetic energy source or for physical contact with a subject.

Another object of this invention is to provide a non-contacting apparatus which non-invasively and continuously monitors a change in the pH level of an individual's blood by monitoring changes in infrared conditions, without the need for a supplemental infrared emitter or other source of supplemental electromagnetic energy or physical contact with a subject.

A further object of this invention is to provide a non-contacting apparatus which non-invasively and continuously monitors changes in the amount of a component substance such as $CO_2$ or $H_2O$ or blood gases present in the exhaled breath by monitoring the changes in the amount of infrared energy emitted by the component being monitored, without the need for a supplemental infrared emitter or other source of supplemental electromagnetic energy or physical contact with a subject.

Another object of this invention is to provide a method for detecting changes in the respiratory condition of an individual by monitoring changes in infrared emissions, without the need for a supplemental infrared emitter or other source of supplemental electromagnetic energy or physical contact with a patient.

Yet a further object of this invention is to provide a method for detecting a change in the pH level of an individual's blood by monitoring changes in infrared emissions, without the need for a supplemental infrared emitter or physical contact with a subject.

Another object of this invention is to provide a non-invasive method for continuously detecting changes in the amount of a component substance such as $CO_2$, $H_2O$ or blood present in expired breath located in a particular area by monitoring the changes in the infrared energy emitted by the component being monitored, without the need for a supplemental infrared emitter or other source of supplemental electromagnetic energy or physical contact with a subject.

The fundamental concepts which are the basis of this invention are adaptable to many medical and non-medical applications. Examples of medical devices which are adaptable from the invention described herein include devices which are capable of measuring $CO_2$ only, $CO_2$ and $H_2O$ vapor only, general body motion and other gases which are exhaled and which indicate various physiologic conditions of a patient.

General body motion may be monitored by a device which senses body movements, such as "micromotion," associated with breathing or other patient activity. Such a device may utilize a single infrared detector comprising a sensor, a signal processing system and, optionally, a microphone of the type used in present baby monitors. Alternatively, the device may employ one or more sensors to generate a matrix of signals capable of being imaged. Signal processing on the matrix of signals is similar to that for a single signal system, except that a higher degree of resolution may be obtained when processing a matrix of signals.

Although this embodiment is applicable to all types of subjects, the monitoring of infants is of particular interest. A number of over-the-counter devices exist that allow parents to listen to crib sounds through a wireless microphone. These monitors are sold by several toy and baby product manufacturers. These monitors serve the function of alleviating parental anxiety by alerting them to situations where the baby vocalizes distress. However, conditions exist in which an infant may be unable to produce audible indication of distress. For those conditions, devices that listen to an infant provide no indication of a problem.

One embodiment of this invention includes a low-cost infant monitoring device using infrared-based micromotion detection that requires no special training or abilities of the caregiver. This embodiment allows the caregiver to monitor infants in distress whether the distress is vocalized or not. Present baby activity monitors only provide capability for vocalizations.

Motion detection can be combined with audio monitoring to produce an enhanced version of present mass-marketed baby monitors. The monitor can be mounted over a crib where it detects motion anomalies (e.g., lack of micromotion and excessive motion) and provides listen-in capability for parents. The enhanced baby monitoring device may transmit this monitoring information to a portable alert device through a radio-frequency (wireless) link.

The invention may also be adapted to sense gases other than those specifically described herein by utilizing the same technology described above. For example, diabetics exhale specific elements which could be monitored to determine a patient's diabetic status. In yet another medical application, certain ketones exhaled by individuals who suffer from liver ailments could be monitored to determine a patient's pathological liver condition.

A high resolution thermographic scanning system utilizing this infrared technology is also contemplated. In addition to apnea detection by monitoring of respiratory components and body motion, this scanning/imaging system could be used, for example, to detect minute temperature gradients on the skin surface. This scanning system may be used either with or without certain drugs which when injected increase the metabolic rate of tumors, thereby making them more visible to an infrared scanning system. The scanner would also provide a single, nonionizing screening for tumors present under the skin. Many other applications which indicate the physiological status of patients are contemplated which sense the infrared absorption peaks of various exhaled gases and elements. As described herein, the signals generated by the various absorption peaks may be converted into useful information adaptable to a wide variety of medical applications.

Examples of non-medical applications which utilize this invention include devices which detect the presence of elements such as methane, ammonia, carbon monoxide, and other toxic and/or flammable elements in the monitored environment. A device which is capable of detecting such elements would be extremely useful for many industrial applications including an early warning detection system for fire fighters. The absorption peaks of anti-oxidants present in automotive and industrial lubricating fluids (e.g. motor oil, transmission fluid, antifreeze, etc.) may also be monitored for analysis. Such analysis would render information relative to the viability of the fluid, indicating when the fluid has deteriorated to the point where replacement is desired or required.

This invention may also be utilized for environmental applications. Concentrations of certain toxic or gaseous elements present in the waste streams of industrial plants or municipal sewer systems may be monitored. Other non-medical applications contemplated include air quality monitoring devices for commercial and residential buildings and breathalizers for detecting blood alcohol content present in a subject's bloodstream.

Further features, objects and advantages of the invention will become apparent to those skilled in the art upon consideration of the following detailed explanation of specific embodiments of the invention, and with reference to the drawings accompanying this specification.

DETAILED DESCRIPTION OF THE INVENTION

Figure 1:
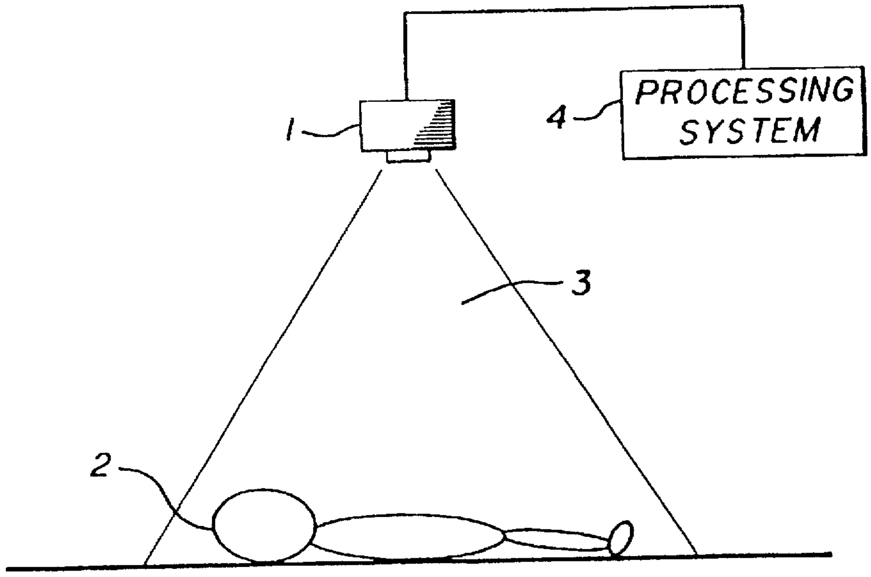
FIG. 1 is a schematic of one embodiment of the monitoring system of this invention.

The monitoring system of this invention, as illustrated generally in FIG. 1, comprises breathing detector 1 and an electronic processing system. Various wavelengths of infrared light emitted from patient 2 in detection region 3 are identified by breathing detector 1. The detector 1 sends signals which correspond to the variation in the infrared wavelengths to processing system 4. Processing system 4 then converts the signals received from detector 1 into a signal which indicates, for example, changes in concentrations of $CO_2$, $H_2O$, pH, blood gases and/or body motion of the subject being monitored present in detection region 3.

Figure 2:
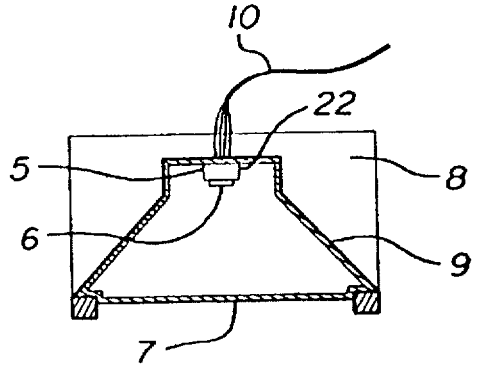
FIG. 2 is a cross sectional side view of an individual sensor head or module which includes refractive optic elements and component and reference sensor elements.

Breathing detector 1 comprises more than one sensor module of the type shown in FIG. 2. Referring now to FIG. 2, each sensor module comprises a sensor 5 capable of detecting changes in infrared energy, preferably a photon sensor or a pyroelectric sensor; a filter 6 capable of passing only infrared energy of desired wavelengths, preferably an optical filter; a lens 7 capable of allowing the sensor to detect a wide area of infrared radiation, preferably a linear or non-linear array lens; thermal insulation 8; sensor module housing 9; and a means for supplying power to the module and transmitting the signal generated by the sensor module from the breathing detector 1 to the electronic processing system 4, preferably by means of a signal/power cable 10.

The detector of FIG. 2 comprises two or more of the sensor modules. One embodiment of the respiratory monitoring system, shown in FIG. 3, utilizes a breathing detector having two sensor modules. One sensor module, which will be referred to as component sensor module 11 with a component sensor 111, responds to changes in infrared energy within the wavelengths of the particular component to be monitored which appear in detection region 12. The component may be, for example $CO_2$ or $H_2O$, in which case the component sensor 111 will be referred to as the $CO_2$ sensor or $H_2O$ sensor respectively. The other sensor module, which will be referred to as reference sensor module 13 with a reference sensor 113, responds to changes in infrared energy wavelengths which may be near but not overlapping those of the component sensor 111, which also appear in detection region 14. The "component" and "reference" designations are used to denote two independent, but associated IR emanation detection channels. In another embodiment, the component sensor module 11 responds as above to the wavelengths of the component to be measured, and also to the same wavelengths of the reference sensor 113. In yet another embodiment, the reference sensor 13, responds to changes in a range of wavelengths that span infrared regions of both the component and a non-component, and the component sensor 111 responds to wavelengths of only the component. Both sensor modules are preferably angled to converge their respective images on image detection plane 15 and are mounted in a commonly shared breathing detector housing 16.

Other embodiments of the invention may comprise a multiplicity of sensor modules in various configurations. The sensors utilized by a multiple sensor module embodiment of the invention may be the same or similar in construction to the sensors illustrated in FIG. 3 or of other suitable constructions, some of which are described herein. In the case of a respiratory monitor, the modules, or breathing detectors should be arranged such that the patient's nose and mouth fall within the detection region of one or more of the detectors. A typical number of detectors could be four to eight. An economically practical upper limit of individual assemblies would likely be 12, although embodiments comprising more than 12 detectors are possible, depending upon the area requirements of the monitoring environment.

Figure 4:
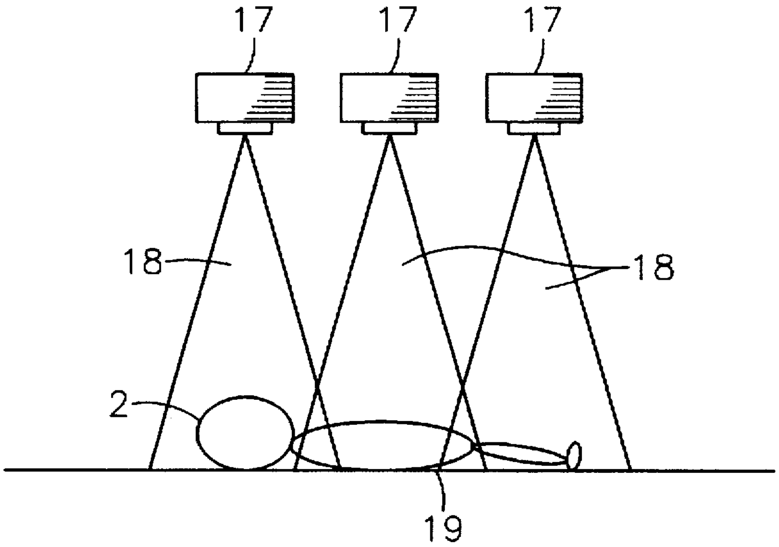
FIG. 4 is a side view of one embodiment of the monitoring system of this invention which utilizes three breathing detectors, refractive optics, and convergent topology.
Figure 5:
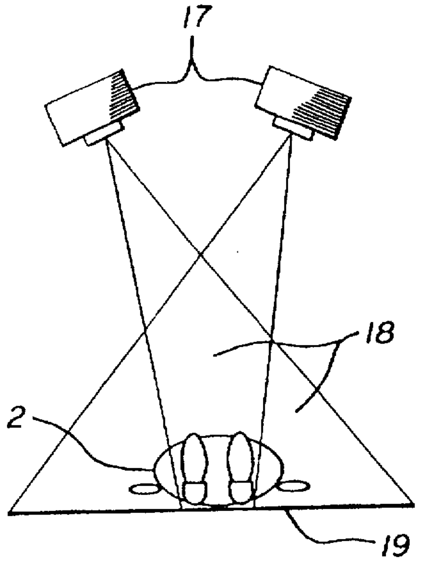
FIG. 5 is an end view of an embodiment of the monitoring system which utilizes two rows, one on each side of the patient, of the type of detector shown in FIG. 4.
Figure 6:
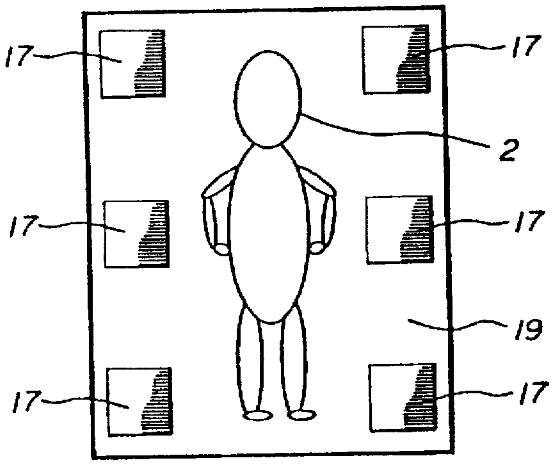
FIG. 6 is a plan view of the monitoring system of FIG. 5.

One embodiment of a respiratory monitor which employs multiple detectors is depicted in FIGS. 4, 5 and 6. This embodiment comprises six breathing detectors 17 each of which cast detection regions 18 onto image detection plane 19. Referring to FIGS. 4, 5 and 6, detection regions 18 cumulatively define a detection or monitored environment in which infrared readings are taken by detectors 17. These arrangements are not unique; other arrangements and quantities of detectors as well as geometries of the detection environments are possible, if not limitless. Generally, however, the size and shape of the environment as well as the size and condition of the patient (from newborn to adult) are factors considered when determining the parameters of the detector arrangement. Numerous configurations of detectors 17 may be utilized, although this choice may be dependent on the size and shape of the monitored environment desired, and the subject being analyzed.

The sensors in the monitor work on the pyroelectric detection principle. Light impinging on the sensor's pyroelectric element produces a change in its temperature. This temperature change, in turn, produces an electric charge output. The charge is delivered to an impedance conversion device, which consists of a resistor to bleed charge and one or more field-effect transistors (FET) or other high-impedance, low-noise amplifiers. The impedance converter and amplifier are usually sealed within the same case as the pyroelectric element for reduction of electromagnetic interference (EMI). The output of the impedance converter and amplifier provides a voltage suitable for further amplification and signal processing.

When thin lens refractive optics are used to focus the infrared energy on the sensor, the size and shape of the sensor's element, along with the characteristics of the optics, will determine the size and shape of the patient sensing area. The sensor may be composed of one of several available materials, depending upon the monitored wavelength and the IR source temperature. Consistent with the present state of sensor technology, and when monitoring for $CO_2$ at the 4.28 micron wavelength, lead selenium (PbSe) is the preferred material for optimizing performance and ease of use. The sensor should be housed in a sealed environment and protected against external influences such as temperature variations, electromagnetic interference, and air-born contaminants. Furthermore, the sensor should be configured so as to sense only specific wavelengths of infrared light. This may be accomplished by forcing incoming light, or infrared energy, to pass through an optical filter, which transmits only a specific band of infrared energy.

One embodiment of this invention takes advantage of a particular $CO_2$ IR electromagnetic radiation absorption line in a region of the spectrum where none of the other major constituents of air significantly absorb such radiation. The center of this particular $CO_2$ absorption line is located at a wavelength of about 4.28 microns and is approximately 0.25 microns wide. Although narrow, the 4.28 micron $CO_2$ absorption line is quite deep. To illustrate this point, consider that there is less than 0.1% transmission of IR energy through a 300 meter path of standard atmosphere at sea level in the wavelength range of 4.17 to 4.34 microns due only to the absorption of atmospheric $CO_2$. In an adjacent region of the spectrum starting at 4.17 microns and extending to about 3.5 microns, there is essentially 100% transmission of IR energy through the same path under the same conditions.

It has been determined that, with an appropriate apparatus, the 4.28 micron wavelength IR absorption characteristic of $CO_2$ can be exploited to enable reliable detection of $CO_2$. When the system is employed to monitor a person's breathing pattern, it functions as a reliable and accurate apnea detector.

In a preferred embodiment, detection of IR radiation in the 4.28 micron wavelength region is accomplished with the use of a lead selenium (PbSe) photoconductive detector. The PbSe detector is a member of the family of photon detectors and has been observed as exhibiting greater sensitivity and ease of use than other presently available detectors. While pyroelectric detectors, or thermal detectors, are generally preferred for use at the longer wavelengths, photon detectors deliver better performance at shorter wavelengths.

The performance of a particular detector, or sensor, can be evaluated from a parametric value known as Normalized Spectral Detectivity (D*). This D* value indicates the smallest amount of radiant electromagnetic energy that can be sensed by the detector, normalized to take into account the detector's electrical bandwidth and active area dependence. Detector D* values often depend on the wavelength of incident electromagnetic energy, the frequency at which the incident electromagnetic energy is chopped, the detector temperature, the detector field of view, and the ambient temperature. The larger the D* value of a particular sensor, the smaller the amount of IR energy that can be sensed. As it relates to the present invention, the ability to sense smaller levels of IR energy directly translates to the ability to reliably detect smaller amounts of $CO_2$ gas. In other words, a larger D* is preferred over a smaller D* value.

The specific D* obtainable is dependent upon how the PbSe detector is applied. Several operating characteristics of an IR detection system that incorporates PbSe detectors can be optimized to maximize the detector D*. The most salient among these operating characteristics are chopping frequency and detector temperature. The higher the frequency at which the incident IR energy is chopped, the higher the D* of the PbSe detector with a peak of the D* value occurring at just under 10 kHz. The D* value of the PbSe detector can also be significantly increased by operating the detector at a lower absolute temperature. PbSe detectors are available that exhibit a D* in the 3 to 4 micron IR wavelength range of up to about $3\times10^9$ centimeter-root hertz per watt (cm-$Hz^{1/2}$/W) at room temperature (300 Kelvin) and with the incident IR energy chopped at 1 kHz. When cooled to 243 Kelvin (K), PbSe detectors can exhibit a D* in the 3 to 4.8 micron IR wavelength range slightly over $1\times10^{10}$ cm-$Hz^{1/2}$/W. When cooled to 77K, PbSe detectors can exhibit a D* in the 3.5 to 5.5 micron IR wavelength range of about $2\times10^{10}$ cm-$Hz^{1/2}$/W.

Figure 3:
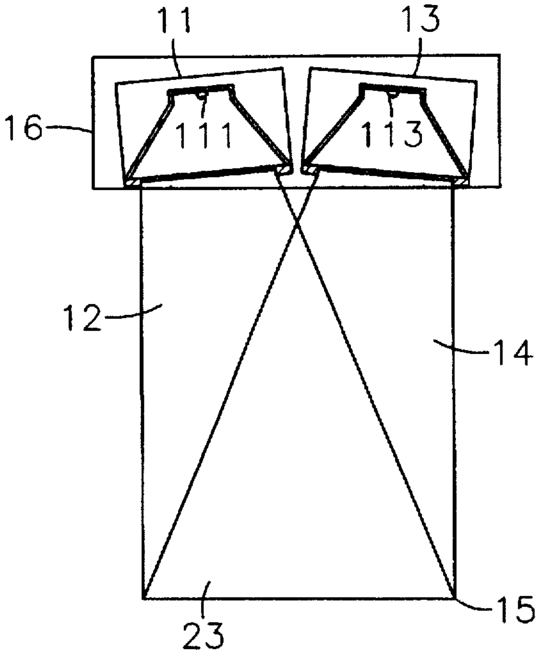
FIG. 3 is a cross sectional side view of a breathing detector comprising individual component and reference sensors, of the type shown in FIG. 2, mounted in a dual sensor assembly housing, and which also employs refractive optics and convergent topology.

When considering the embodiment designed to detect changes in the presence of $CO_2$ the filter for the reference sensor passes infrared energy in about the 8 to about 14 micron range. The $CO_2$ sensor's filter passes energy in about the 14 to about 16 micron range. This covers the major 15.3 micron $CO_2$ absorption peak. The $CO_2$ sensor's filter may also pass infrared energy in about the 4.0 to about the 5.0 micron range which may include other $CO_2$ absorption peaks, such as the peak at 4.28 microns. Wavelengths in any desired range may also be included by the judicious selection of filter material. However, the 14 to 16 micron range contains the most energy for detecting $CO_2$ in a relatively low temperature environment (between about 60° and about 100° F.). The amount of energy produced in about the 4.28 micron range by a blackbody radiator at room temperature is significantly less than that produced in the 14 to 16 micron range, which is why the more sensitive PbSe detector is preferred at these shorter wavelengths. Available energies are shown in Table 1 below for two $CO_2$ absorption bands, an $H_2O$ absorption band, and a wide-range reference detection band. The last column shows the advantage of the longer wavelength $CO_2$ band by listing the ratio of the 14 to 16 and 4.19 to 4.45 micron bands.

convergent topology. The component sensor detects infrared energy in the absorption spectrum of the desired component, for example $CO_2$. The reference sensor detects infrared energy in a band near that of the component sensor but not including the energy of the component (e.g., $CO_2$). Enhanced signals may be attained by means of reflective, refractive, or a combination of reflective and refractive optics. FIG. 3 shows two sensor modules: component sensor module 11 and reference sensor module 13. In this embodiment, component sensor module 11 detects a range of wavelengths with the exception of wavelengths corresponding to $CO_2$ absorption, and reference sensor module 13 detects wavelengths corresponding to $CO_2$. The arrangement depicted in FIG. 3 represents a convergent topology in which the detection zones of each module, 12 and 14, individually converge on image plane 15. In the case of an apnea monitor, all patient activity must be contained within convergent region 23 for this topology to operate most accurately.

The "component" and "reference" designations can be thought of as denoting two independent, but associated IR

TABLE 1

Available Energy For Several Infrared Bands, Including $CO_2$ and $H_2O$

| | Comparison of Available Energy Through Various Spectral Windows (Watts/cm²) | | | | |
|---|---|---|---|---|---|
| Blackbody Temperature (°C.) | $CO_2$ (4.19–4.45 μm) [A] | $H_2O$ (5.5–6.5 μm) | Wide-Range Motion (8–14 μm) | $CO_2$ (14–16 μm) [B] | Longer $\lambda CO_2$ Advantage [B/A] |
| 20 (68° F.) | $0.755 \times 10^{-4}$ | $1.3 \times 10^{-3}$ | $1.53 \times 10^{-2}$ | $3.7 \times 10^{-3}$ | 49 |
| 25 (77° F.) | $0.914 \times 10^{-4}$ | $1.5 \times 10^{-3}$ | $1.66 \times 10^{-2}$ | $4.0 \times 10^{-3}$ | 44 |
| 31 (87.8° F.) | $1.140 \times 10^{-4}$ | $1.8 \times 10^{-3}$ | $1.81 \times 10^{-2}$ | $4.2 \times 10^{-3}$ | 37 |
| 34 (93.2° F.) | $1.270 \times 10^{-4}$ | $2.0 \times 10^{-3}$ | $1.89 \times 10^{-2}$ | $4.3 \times 10^{-3}$ | 34 |

Figure 7:
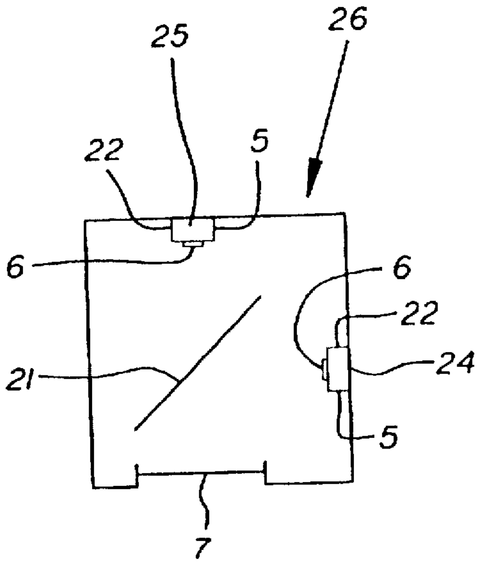
FIG. 7 is a cross sectional side view of a composition detector which utilizes refractive and reflective optics.

Referring now to FIG. 2 for the refractive optical embodiment of this invention and FIG. 7 for the combination reflective and refractive optical embodiment, filter 6 is usually placed between pyroelectric element 5 and lens 7 in a system using refractive optics (thin lens or Fresnel lens optics) or between sensor 5 and lens 7 in a system using refractive optics (thin lens or Fresnel lens optics) or between sensor 5 and reflector components 221 in a reflective optic system. Filter 6 may be mounted directly to housing 22 of the pyroelectric sensor (as a window) or movably mounted along the optical path in the sensor module housing 9. However, if optical filter 6 is placed close to sensor 5, filter 6 can be made smaller in size and therefore less expensively. Materials used for the filter include doped silicon or germanium, the former being less expensive.

One embodiment of a refractive optic sensor module is shown in FIG. 2. The module consists of sensor 5 in metal sensor housing 22 with optical infrared filter 6 placed as a window for admitting light to the element, fresnel lens 7, plastic or metal module housing 9, and thermally insulating material 8 around the housing for minimizing the effects of external ambient temperature changes.

To enhance the detection of the desired component signal and cancel the signal corresponding to energy from other sources, two sensors, the component and reference sensors, are required to focus on the same area. This is known as emanation detection channels. For example, in the previously described embodiment employing PbSe detectors for shorter wavelength applications, one detection channel is sensitive only to IR energy in a narrow band about the 3.9 micron wavelength. The "reference" designation is given to this channel because the IR energy detected at the 3.9 micron wavelength is virtually unaffected by the presence of $CO_2$ gas in the channel's field of view. The other channel—"component" channel—is sensitive to IR energy in a narrow band about the 4.28 micron wavelength. This channel receives the "component" designation because the presence of the $CO_2$ component in the scene directly effects the magnitude of IR energy detected at the 4.28 micron wavelength. Other than the fact that the reference channel is unaffected by $CO_2$ gas in the scene, it responds to IR radiating from the scene in the same relative way as the component channel responds. As will be more fully discussed, the reference and component channels for this embodiment incorporate identical scanning schemes to produce temporally and spatially overlapping thermographic or IR images of a target scene.

Figure 8:
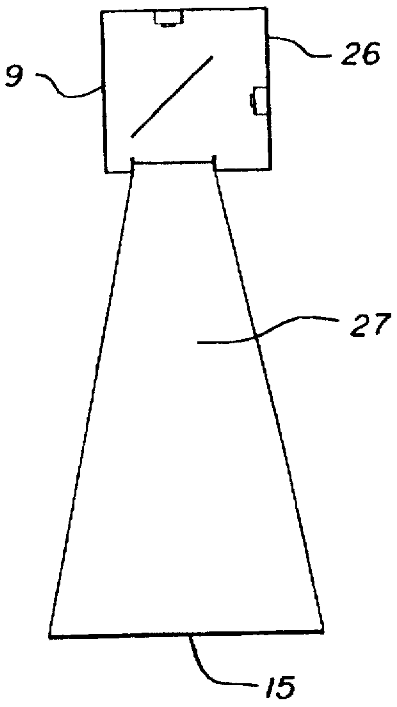
FIG. 8 is a schematic depicting the side view of the composition detector of FIG. 7 which further utilizes collinear topology.

An optical system for collinear topology is shown in FIG. 7. Detector 26 contains both component (such as $CO_2$) and reference sensors 24 and 25 respectively. In FIG. 7, detector 26 is shown to consist of a common lens 7, such as a nonlinear lens array, with partial mirror 21 to split the light to both reference sensor 25 and $CO_2$ sensor 24. As shown in FIG. 8, both sensors always image the same area 27 regardless of sensor distance or orientation. This eliminates the need to maintain perfect convergence of two independent sensor modules as required by the convergent topology shown in FIG. 3. Thus, the collinear optical system is the preferred topology for the monitor of this invention.

For either of the topologies, each sensor produces a voltage signal proportional to the change incident infrared energy of their respective bands. Referring again to FIGS. 1 and 2, the output of each sensor is independently passed to processing system 4, where the undesired signals will be removed and further filtering will enhance the signal corresponding to the variation in the component to be monitored, for example, $CO_2$.

$CO_2$ gas within an imaged area or target scene can be detected by employing PbSe detectors or PbSe detector arrays as the sensors 111 and 113 (FIG. 3) in combination with IR filtering and IR scanning. Direct thermal and mechanical connections of appropriate optical filter devices to the detectors of the apparatus accomplish optimum narrow band pass IR filtering centered at the desired 3.9 and 4.28 micron wavelengths. The filter devices are sized and positioned such that they completely encompass the IR sensitive or active areas of the detectors.

The sensitivity required to detect changes in infrared energy in bands such as $CO_2$ demands maximum optical as well as electronic sensitivity. The best method of increasing sensitivity while maintaining highest signal-to-noise ratio is to maximize the gain closest to the measurement point. To achieve this maximization, high-gain optics should be used. Potentially, reflective optics offer higher gain than do refractive optics (i.e., more light is delivered to the sensor element with reflective optics). This is due in part to lower absorption of the reflective elements and also to the ability of creating larger equivalent apertures compared with refractive elements.

Achieving wide-angle coverage of the area where the patient is being monitored, while also striving to maintain high light-gathering capacity, is difficult with thin-lens (refractive) optics. The aperture must remain wide to pass sufficient light. A practical limit is reached as the lens opening is enlarged since f-stops smaller than about 0.6 are not attainable with present technology. Achievable limits on a 0.9 inch focal length Fresnel lens is a diameter of about 1.5 inches. This yields an f-stop of about 0.6. A shorter focal length lens of the same diameter would actually admit less light. Another option for achieving wide-angle view using refractive optics is to enlarge the area of the pyroelectric sensing element. An achievable size of about 7 mm×7 mm for the pyroelectric yields an imaging area of about 7.7 inches at a 25 inch subject distance with a 0.9 inch focal length Fresnel lens. With the same size pyroelectric element, an 0.5 inch focal length lens would yield about 14 inches of detection area. The lens diameter would decrease to about 0.83 inch diameter, which is about half of the light-gathering power.

FIGS. 2 and 3 show detectors using refractive optic elements for defining a detection region. Each embodiment employs a nonlinear lens array 7. Alternatively, each embodiment shown in FIGS. 2 and 3 may be outfitted with reflective optics. It is also possible to create an optical system consisting of both refractive and reflective components as shown in FIGS. 7 and 8 for achieving a wide-angle view with high light-gathering power.

Figure 9:
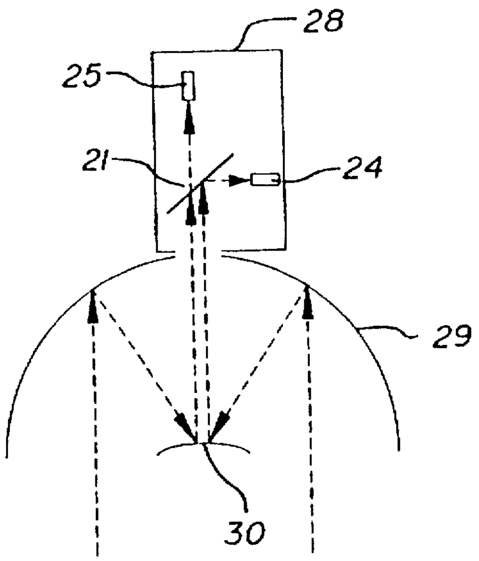
FIG. 9 is a schematic depicting the side view of one embodiment of a detector of this invention which utilizes reflective and collinear optics only.

FIG. 9 illustrates a collinear sensor topology using only reflective optical elements. The broken lines in FIG. 9 depict the path which the infrared light follows as it is reflected from surface to surface prior to reaching the appropriate sensor. This embodiment comprises collinear detector 28 (of the type depicted in FIG. 7 except that there is no refractive lens at the opening to the detector) with sensor modules 24 and 25 and partial mirror 21 (but without nonlinear lens array 7); parabolic (or other shaped) reflective surface 29, which focuses surrounding infrared light; and mirror 30, which in turn reflects infrared light into breathing detector 28. Mirror 30 may be optionally linear or curved. As shown in FIG. 9, partial mirror 21 allows certain wavelengths to pass through to sensor module 25 while reflecting other wavelengths to sensor module 24. Other combinations of nonlinear reflective surfaces are possible as well as combination of reflective and refractive elements. It is possible to design the reflective optical surfaces to reflect specific wavelengths so that part of the wavelength filtering may be performed in the optical components of the particular monitoring system.

Other non-imaging optics are potentially useful for the monitor of this invention since a well-focused optical image is not required. An integrating sphere used with a collimator or other reflective or refractive optical elements could provide wide-angle coverage with relatively high light-gathering power.

For all embodiments of this invention, the most accurate data collection will occur if the subject being monitored remains within the monitored environment during monitoring. One manner of assuring that the subject remains within the detection region is to constrain him in an enclosure. In the case of the apnea monitoring system, an enclosure may be utilized to confine the subject to the monitored environment. The enclosure may be open on the top, allowing for unobstructed breathing, a view of the outside, and a means by which the patient may interface with other persons. Many variations are possible for restraining the individual in fixed area. Common examples may be beds, cribs, car seats, chairs and the like.

Processing system 4 of FIG. 1 receives and processes the signals from the reference and component sensors to produce a signal which corresponds to the desired information. FIG. 1 depicts processing system 4. In the case of the apnea monitor, this system performs the following digital signal processing actions: sensor signal prefiltering and digitization, subtraction of the general reference signal from the component signal, frequency and/or time-based analysis and parameters extraction of the resultant signal, comparison of the measured signals with known signals from normal and abnormal patients, display of important system variables, interface with user input system (keyboard, switches, etc.), storage of data, and output of data to an external device. Some of these functions may be located locally in the sensor module(s). A communicator module may also be included that sends a distress signal to a remote location for indicating an apnea event to the caregiver. This communicator may call by telephone or transmit by radio-frequency or other medium to a remote indication module.

Figure 10A:
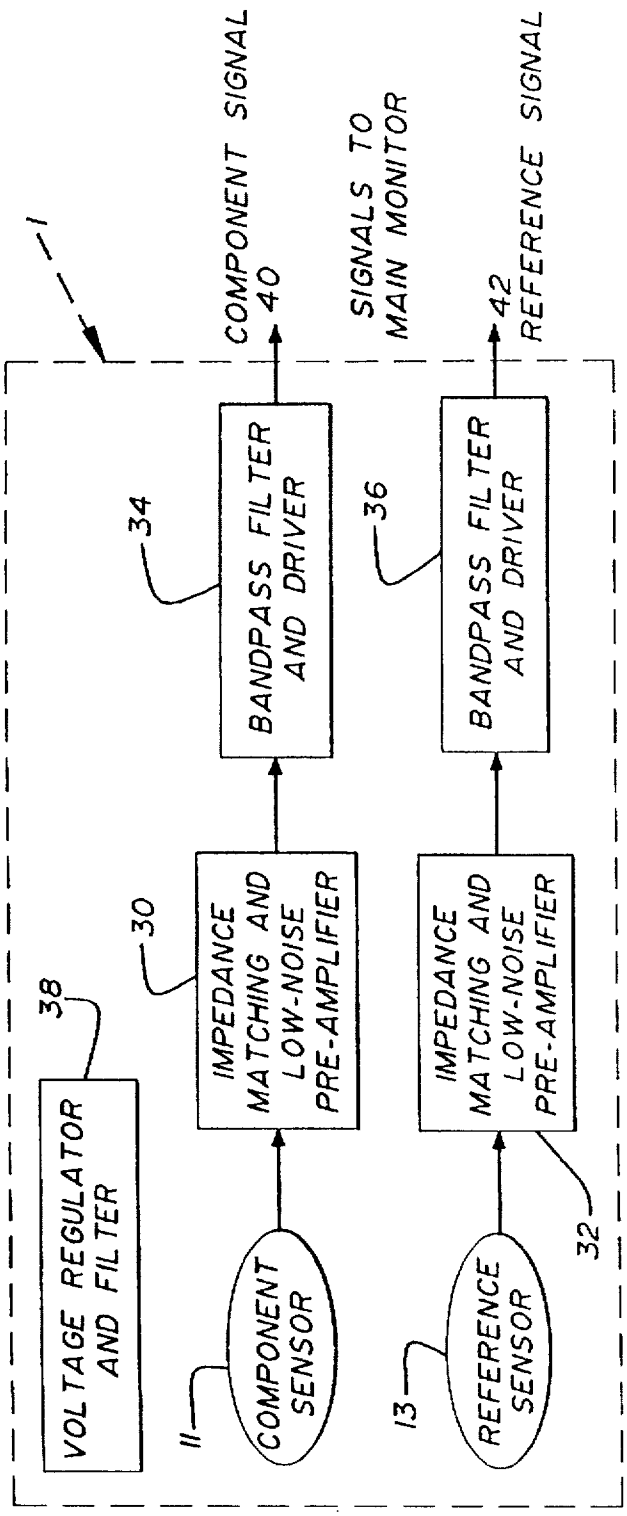
FIG. 10A is a block diagram of one embodiment of the sensor module or head portion of the signal processing system which processes the infrared energy signals received by the component and reference sensor to the input of the main signal processor.

One embodiment of processing system 4 is depicted in block diagram form in FIGS. 10A, 10B, 10C and 11D. FIG. 10A depicts a typical detector 1 which comprises a component sensor 11 and reference sensor 13, pre-amplifiers 30 and 32, filters/drivers 34 and 36, and voltage regulator and filter 38 all of which generate the component and reference signals N, 40 and 42, which are the input signals to main signal processor 50 shown in diagrammatic detail in FIGS. 10B and 11. Signal processor 50 comprises input buffers and amplifiers 52, 54 and $N_1$, bandpass filters 56, 58 and $N_2$, gain-stage amplifiers 60, 62 and $N_3$, analog multiplexer 64, analog-to-digital converter 66, microprocessor system 68, user interface and local alarm 70, storage system for event analysis 72 and radio-frequency link to remote alarm device 74.

Reference numbers, N, $N_1$, $N_2$ and $N_3$, denote additional signals and components which would be included in the processing system for each additional detector 1 which is incorporated in any particular embodiment of the invention. In this embodiment of processing system 4, each detector 1 would require a corresponding input signal N and components $N_1$, $N_2$ and $N_3$.

Microprocessor system 68 comprises digital signal processor 76, microcontroller 78, and memory device 80. The basic logic utilized for this embodiment of microprocessor system 68 is depicted in the flow chart of FIG. 11. Overlapping signals 100 from analog-to-digital converter 66 are assembled into a full signal at 102, generating sensor signal 104. Sensor signals 104 are reconstructed using neural networks or other processing algorithms to form true component signals 108 at 106. Breathing parameters are extracted from true component signals 108 using wavelet analysis or similar means at 112 to generate signal 116. Breathing patterns from signal 108 are matched with known anomalies at 114 to generate signals 118. Signals 116 and 118 are processed using threshold, fuzz-logic, neural networks or similar processing technique at 120 to determine if an alarm or other desired output condition exists which is expressed and communicated by signal 122.

Figure 10C:
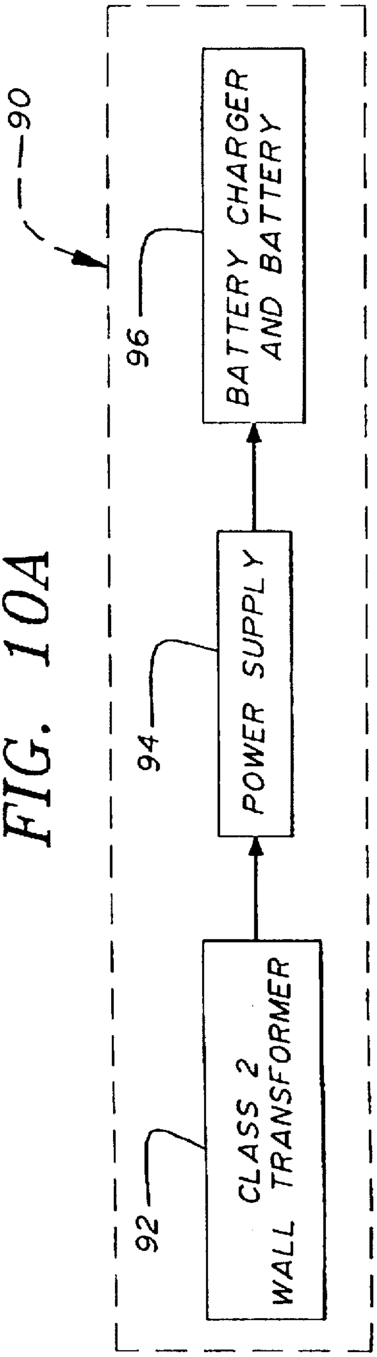
FIG. 10C is a block diagram of one embodiment of the power supply which supplies suitable power to the monitor.
Figure 10B:
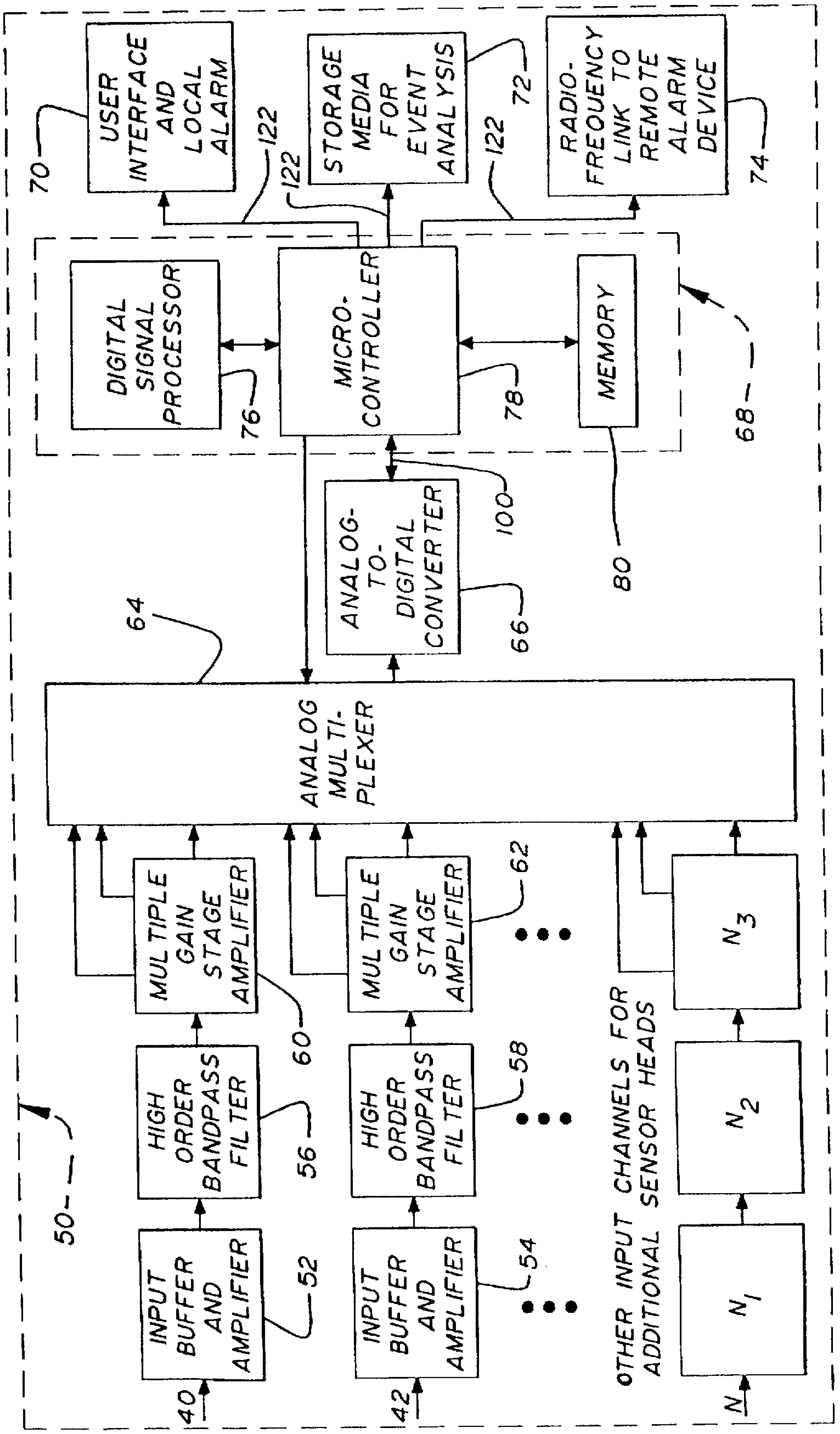
FIG. 10B is a block diagram of one embodiment of the main signal processing portion of signal processing system which processes signals received from the sensor module or head which produces the desired output signals.
Figure 11:
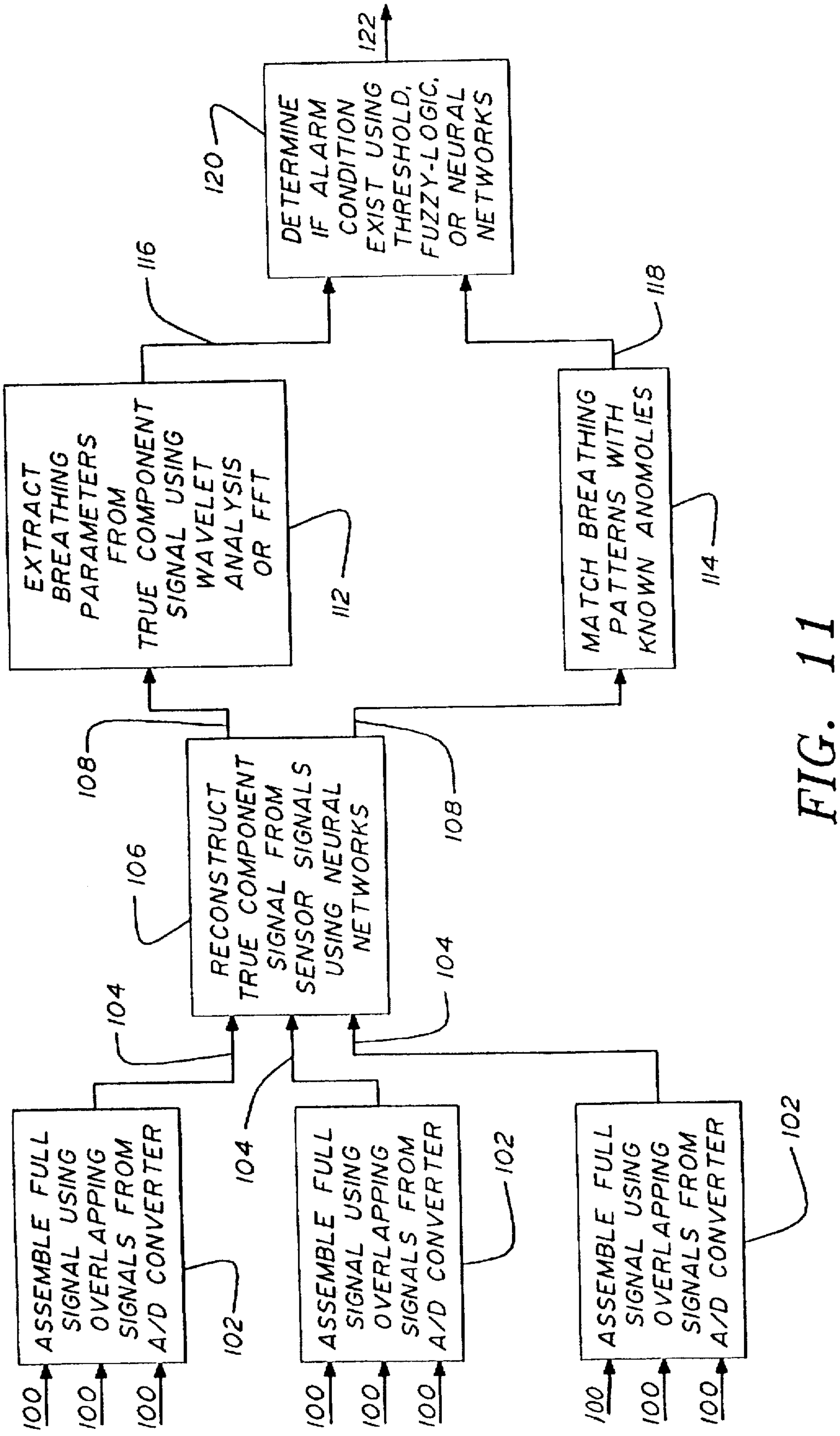
FIG. 11 is a block diagram of steps of signal processing conducted within the microprocessor system of FIG. 10B which includes microcontroller, digital signal processor and memory of the system.

FIG. 10C depicts the power supply system used in one embodiment of the invention. Power supply system 90 comprises class 2 wall transformer 92, power supply 94 and battery charger and battery system 96.

Generally, processing system 4 derives a new signal or signals received from detector(s) 1. Several methods for deriving the new signal(s) representing changes in the component substances being analyzed by the monitor may be enlisted. Such methods include simple mathematical subtraction, weighted subtraction, non-linear functions, artificial neural networks, fuzzy logic or a combination of these methods.

Simple mathematical subtraction may be accomplished by calculating the mathematical difference between the component and reference signals. The resultant value has a major portion of the non-component variations removed.

Weighted subtraction is similar to single subtraction except that either one of the sensor signals is multiplied by a weighting factor. The weighting factor is calculated by taking the ratio of both signals averaged over a selected time interval.

In the non-linear function method a mathematical function is derived such that, by its application to two or more unmodified sensor signals, the desired component is enhanced. The function may operate on one or more of the sensor signals or on all of them together. The function may contain non-linear mathematical equations, operators, or describing functions. A separate system of equations may be present to periodically tune the mathematical function so as to keep it current with the behavior of the sensors, environment, and electronics.

An artificial neural network (ANN) may be used to reconstruct a new signal based on two or more sensor signals. The ANN may consist of an input and an output layer of neurons, and may contain a hidden layer of neurons as needed to properly recreate the true component signal under a variety of situations and environmental conditions. Once the ANN is trained on numerous and varied examples, an accurately reconstructed signal can be derived even under many new conditions for which the ANN has not been specifically trained.

Fuzzy logic may be utilized within a system which comprises rules operating a fuzzy variable, derived from sensor signals, to obtain a new signal with motion and/or other undesirable features removed. This fuzzy-logic system is especially applicable to systems for which a specific mathematical model is difficult to derive.

The above-mentioned methods may be combined to create a system that derives a satisfactory representative signal of the component of interest.

In another embodiment of this invention, expired water vapor can be measured by the same or similar method used to measure expired $CO_2$. Like $CO_2$, $H_2O$ absorbs infrared energy at particular wavelengths. A component sensor (in this embodiment the $H_2O$ sensor) outfitted with an optical filter to pass wavelengths in about the 5.5 to 6.5 micron range allows detection of changes in water vapor. Patient motion can be removed by subtraction of the reference sensor signal (as in the case of $CO_2$) from the $H_2O$ signal. The $H_2O$ signal can be used as a reference signal that indicates the depth of breathing (i.e., the volume of expired air). If the $H_2O$ sensor is used in conjunction with a $CO_2$ sensor, a derived signal, which is the ratio of the $H_2O$ and $CO_2$ signals, can be used to track the concentration of $CO_2$ in the expired breath. The concentration of $CO_2$ will only change if the amount of $CO_2$ leaving the blood stream (into the lungs) has changed, which indicates a change in blood pH. $H_2O$ concentration detectability provides the means for rapidly and continuously monitoring trends in blood pH levels.

A third sensor and $H_2O$ band optical filter (acting in about the 5.5 to 6.5 micron range), would be all that is required to include the $H_2O$ measurement with sensory systems described above. For the collinear optics system, a second mirror is required for a three-way split of the incoming light: one beam for $CO_2$ detection, one for $H_2O$ detection, and one for reference.

In another embodiment of this invention, general body motion of a subject located in the monitored environment may be detected. This motion may be in the form of micromotion. Such micromotion may be the chest movements of the subject which may signify breathing. However, any general body movement of the subject may be detected. Micromotion may be sensed by a single sensor without the need of two sensor channels as required when monitoring respiratory components such as $CO_2$ and $H_2O$, or the device may employ one or more sensors to generate a matrix of signals capable of being imaged. Signal processing on the matrix of signals is similar to that for a single signal system, except that a higher degree of resolution may be obtained when processing a matrix of signals.

Unlike the foregoing embodiments, the device utilizes a single sensor, or sensor array (including two-dimensional arrays) as will be further discussed, which may detect changes in infrared energy which signifies and corresponds to changes in micromotion of the subject. The sensor preferably comprises a pyroelectric crystal and optical filter which admits a selected range of infrared wavelengths. For detecting motion, such wavelengths are in about the 8 to about the 16 micron range. See Table 1 for the available energy for this infrared band. Upon detecting a change in micromotion, the sensor (or sensor array) generates a first or input signal which is received by a processing system, which converts the input signal into a second or output signal. The output signal signifies the micromotion of the subject within the monitored environment. The output signal may signify any change in motion including an increase, decrease or absence of micromotion of the subject in the monitored environment. The processing system utilized in this embodiment may be similar to the processing system disclosed in FIGS. 10A, 10B and 10C. The output signal can be used as the input signal to any desired output device such as a digital display or an audio alarm which would alert the caregiver or person monitoring the subject to a change in the subject's condition.

This motion detection embodiment may optionally be combined with an audio detection device similar to the wireless microphone devices now available for monitoring sounds of an infant in a remote area such as a nursery. The audio detector may be integrated with the motion detector wherein the audio detector comprises a microphone in operative communication with the monitored environment. The microphone should preferably be sensitive to and capable of detecting sound waves produced by barely audible sound in the monitored environment. Upon detection of the sound, the microphone produces an output signal to the motion detector's processing system, wherein the processing system is capable of converting and, as necessary, amplifying the microphone's output signal into a signal which signifies the sound present in the monitored environment. The converted signal may be fed to a speaker located within audible range of the caregiver or person monitoring the subject.

A set of experiments were performed to test the hypothesis that human breathing could be detected non-intrusively by measuring the absorption of $CO_2$ from exhaled breath in an infrared energy field. Gaseous $CO_2$ has known absorption peaks in the infrared energy spectrum between about 4 and 16 microns. By measuring the changes in energy level at one or more of these absorption bands due to changes in $CO_2$ from exhaled breath, breathing can be detected and measured. The component sensor (in this case the $CO_2$ sensor) is also sensitive to changes in the infrared energy level due to motion. A second sensor, the reference sensor, detects a wider energy spectrum, which includes the motion of the patient, and provides a "background" motion signal which can be subtracted from the $CO_2$ signal to obtain a "$CO_2$" only signal.

The natural infrared energy emanating from the subject provided the passive infrared energy source. A detector assembly, consisting of two pyroelectric detectors, each embedded in a block of polystyrene for temperature stability, was constructed. One detector had about a 14.2 to 16 micron transmissive $CO_2$ filter and the other had a wide 8 to 14 micron transmissive "motion" filter. Both sensors were adjusted to be convergent on the same area. The $CO_2$ sensor was very sensitive to changing $CO_2$ concentrations in the path between the infrared source (the subject) and the detector but is also sensitive to motion. The reference sensor was sensitive to general motion only. As both sensors are sensitive to motion, the motion component could be then "subtracted" from the $CO_2$ signal, yielding a signal dependent only upon $CO_2$ concentration changes.

The detector assembly was placed 31 inches above the subject's face. All data were gathered with the subject looking into the detector assembly. Each sensor was adjusted so that it imaged an area about 10 sq. in. about the subject's mouth and nose.

The subject was an adult male, age 43, in good physical condition. For a typical breath, the average adult male has an inspired and expired volume (tidal volume) of 500 ml, with a neonate's tidal volume being as small as 8–10% of this volume (40 to 50 ml). The experiment was conducted with the subject inspiring and expiring a volume of between 29 and 69 ml with an average of 46 ml, approximating that of neonate.

Figure 12:
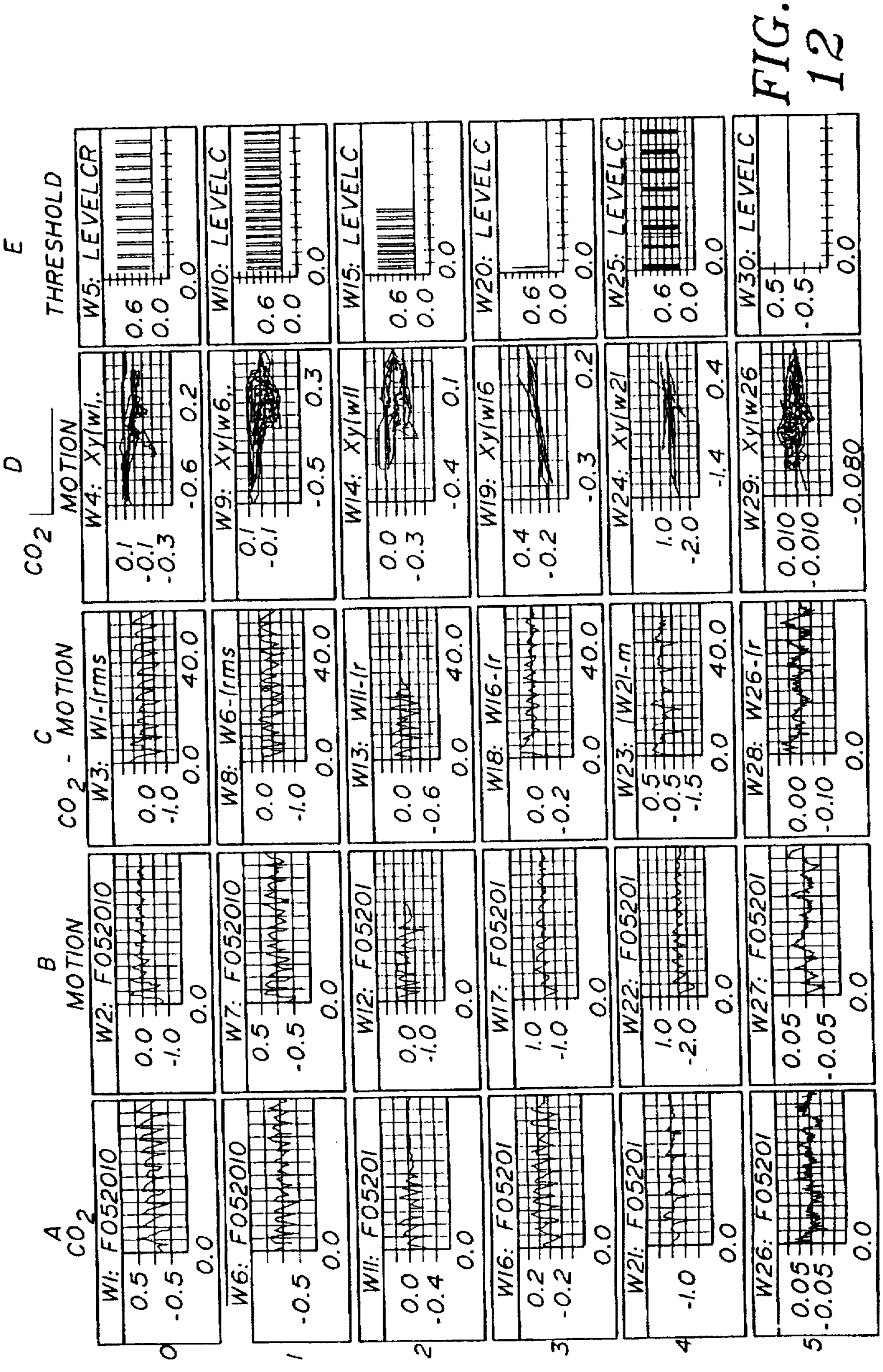
FIG. 12 graphically depicts experimental results.

FIG. 12 graphically depicts the data corresponding to the experimental results. The graphs are divided into columns and rows. Each column represents a signal, either directly from a sensor or mathematically derived from one or more sensor signals. Each row represents a condition under which data were taken. A description of each column is as follows:

TABLE 2

| Column # | Variable Name | Variable |
|---|---|---|
| A | $CO_2$ | Filtered signal from $CO_2$ sensor |
| B | Motion | Filtered signal from reference motion |
| C | $CO_2$-Motion | $CO_2$ Motion signal |
| D | $CO_2$ vs Motion | $CO_2$ signal plotted against Motion signal |
| E | Threshold | Threshold signal where $CO_2$-Motion signal is above a predetermined threshold value |

The $CO_2$ and Reference signals have been filtered to remove high frequency noise. The signal of interest is the $CO_2$—Motion signal. Column D, the plot of $CO_2$ against Motion, is an indication of the correlation of the two variables. Highly correlated data would show up as a diagonal plot. The $CO_2$ and the Motion signals should not normally be correlated, unless they are both measuring large amounts of motion.

Data was taken under various conditions. Each condition is a row number in FIG. 12 ranging from 0 to 5. The conditions are given in the following table.

TABLE 3

| Row # | Condition |
|---|---|
| 0 | Breathing every 5 sec. |
| 1 | Breathing every 2 sec. |
| 2 | Breathing every 2 sec. for 28 sec., followed by 30 sec. with no breathing |
| 3 | Breath held, slight movement of head side to side (for motion cancellation) |
| 4 | Side to side motion, no breathing, external $CO_2$ every 5 sec. |
| 5 | Sensor noise, no subject in field of view |

Column E, the threshold signal, graphically represents the results of each condition under which data was taken. Here, each occurrence of breath is represented by two closely spaced vertical lines, one for the $CO_2$—Motion signal going below the negative threshold and one for the signal recrossing the negative threshold. Accordingly, the results of this analysis illustrates that breathing, approximating that of a neonate, could be consistently and correctly non-intrusively detected.

Much of the discussion thus far has focused on the use of non-imaging single element detectors. However, imaging techniques can also be employed to obtain high resolution monitoring of the target scene, or monitored environment 101, with the only difference being the added concept of imaging to generate a matrix of signals from one or more sensors. A common goal of imaging systems is to construct a two-dimensional image of a scene defined by the desired field of view. Imaging optics (lenses, reflectors, apertures, etc.) build the image by mapping points of the target scene, or object, into points of the image without relative spatial distortion. To construct such an image, a matrix of signals must be constructed with each signal representing a pixel of the image. The matrix of signals, when constructed in the form of a component matrix and a reference matrix, can be analyzed to monitor the respiration of a subject within the monitored environment, and thereby serve as an apnea detector.

Figure 13:
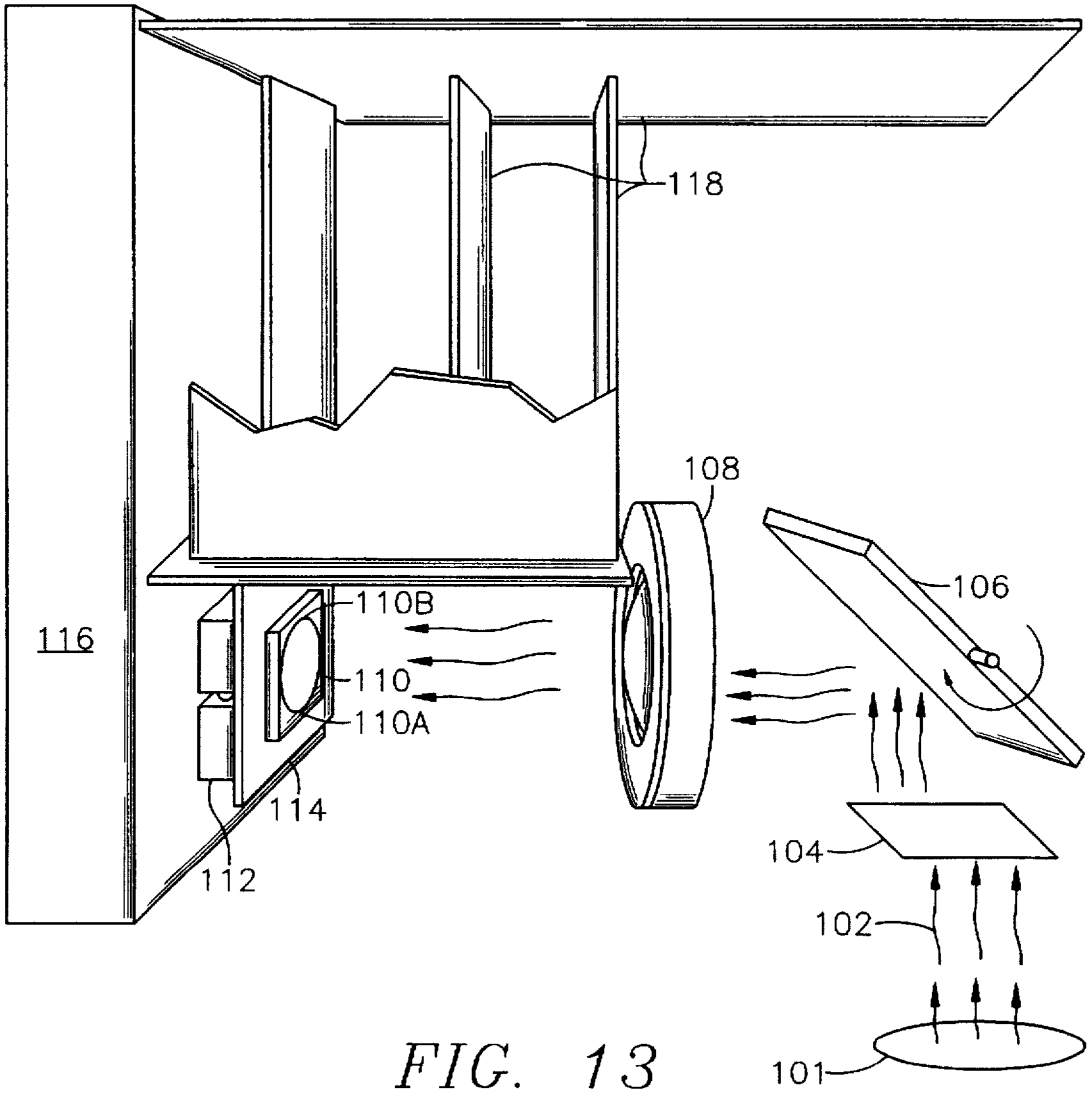
FIG. 13 is a side view of an imaging embodiment of the invention.

FIG. 13 illustrates a preferred embodiment of the present invention which utilizes imaging optics and multisensor, one-dimensional arrays to generate a matrix of signals for each sensor array where each signal in the matrix represents sensed infrared energy within a particular sensor's instantaneous field of view (IFOV). Infrared energy, generally illustrated at 102, eminating from the monitored environment passes through aperture 104 and is reflected by a rotating reflector 106, such as a doublesided, gold plated mirror, through optical lens 108 where the infrared energy is directed onto a detector assembly 110. The reflector 106 rotates in a clockwise direction and reflects infrared energy across the detector assembly 110 in a bottom 110A to top 110B manner. In other words, as the reflector 106 rotates in a clockwise direction reflected infrared energy is first received at the bottom 110A of the detector assembly. As the reflector 106 continues its clockwise rotation, reflected energy eminating from a particular point in the monitored environment 101 will travel upward along the detector assembly 110 toward its top 110B. It will be appreciated that by reversing the rotational direction of the reflector 106 the reflected target scene energy will travel across the detector assembly 110 from top 110B to bottom 110A.

Figure 14:
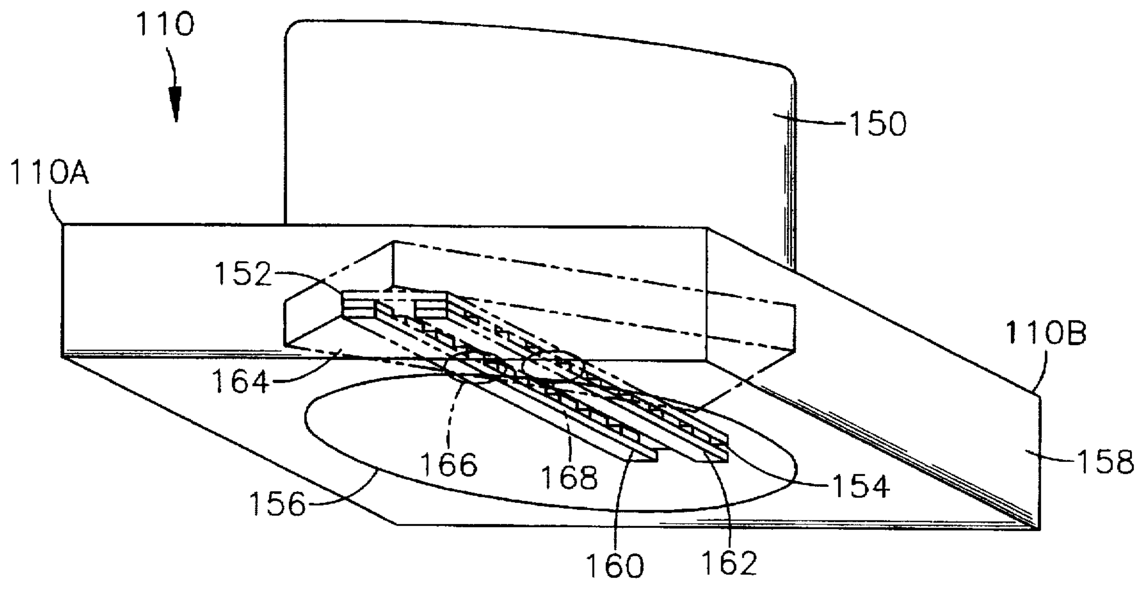
FIG. 14 is a view of an embodiment of the sensor assembly.

The detector assembly 110 is secured in position by means of a clamp 112 attached to a structural support member 114. As shown in FIG. 14, the detector assembly is fitted with a thermal stub 150 which passes through an aperture (not shown) in the support member 114. When inserted through the support member aperture, the thermal stub 150 provides a convenient place for the clamp 112 to securely hold the detector assembly 110. The thermal stub 150 is of sufficient length to extend beyond the clamp 112 and establish contact with a heat sink 116 for dissipation of heat from the detector assembly 110. Circuit boards and electronics, shown generally at 118, provide the electronics necessary to control data collection and to process the data once collected.

FIG. 14 illustrates the detector assembly 110 in greater detail. Mounted to a detector substrate 152 are two one-dimensional arrays of detector/sensor elements 154. The arrays 166, 168 are in parallel relation to each other. One array of elements provides data signals for the reference channel and the other provides data signals for the component channel as previously described. Although the embodiment of FIG. 13 encases both channels of detectors within a single casing 158, it will be understood that the detector arrays 166, 168 may be employed in separate detector modules similar to those depicted in FIGS. 3–6. In this embodiment of FIG. 13, ten detector elements 154 are employed in each array 166, 168. However, it will be understood that any number of elements may be employed and that placement of the elements within the detector assembly 110 is not limited to a one-dimensional arrangement. For example, two-dimensional arrays having ten rows containing ten elements each may be employed to achieve a 10×10 two-dimensional arrangement of each detector channel. The geometry and total number of elements 154 in each array will affect the particular scanning method employed, as will be more fully described.

With continued reference to FIG. 14, infrared energy enters the detector assembly 110 through an IR window 154 in the detector case 156. The IR energy is first received by IR filters 106 and 162 which bandpass filter the energy so that the energy received by the sensors 154 contains only wavelengths of interest. Particular types of sensors 154 are cooled by means of a solid state, thermoelectric cooler located on one of the control and processing boards 118. The thermal stub 150 establishes contact with the heat sink 116 and is used as the cooler hot plate to sink heat from a cooler cold plate 164 and transfer the heat to the heat sink 116. Heat transfer between the sensors 154 and cooler cold plate 164 occurs by way of the detector substrate 152. As previously discussed with regard to PbSe sensors, cooling functions to increase the sensors' sensitivity (D*).

In operation, IR energy is reflected off of reflector 106 so that the energy passes through lens 108 where it is directed onto the IR window 156 of the detector assembly 110. It will be appreciated that the rotational movement of the reflector 106 serves a chopping function to improve the sensitivity (D*) of the sensors 154. Although a two-sided reflector 106 is illustrated in FIG. 13, it will be understood that many modifications to the reflector 106 may be made without departing from the spirit of the invention, the primary functions of the reflector 106 being to alternatingly reflect IR energy from the monitored environment 101 toward the detector assembly 110. For example, three, four, five, six, and other multi-sided reflectors may used in place of the two-sided reflector 106 of FIG. 13. It will be further understood that any means of chopping and any means of scanning may be employed. In this sense, the reflector 106, if used, need not move at all. As an alternative to rotating the reflector 106, it may instead be rocked within a predetermined arc for reflecting IR energy onto the detector assembly 110.

Since the reflector 106 of FIG. 13 is rotating, energy from particular points in the target scene will be swept across each of detector arrays 166, 168 so that there is a slight lag between the time when array 166 first receives energy from a particular line in the monitored environment 101 and when array 168 receives energy from that same line. In the embodiment of FIG. 13, the reflector 106 rotates at a rate of 11 rotations per second and all of the detectors 154 of each array 166, 168 are read every 250 microseconds as IR energy is received and sensed by the detectors 154, so that each channel (component and reference) builds a 10×22 matrix of signals. The signals of each matrix are already spatially overlapping due to the placement of the arrays 166, 168 in relation to each other. To enable temporally overlapping matrices, the signals are time shifted by the time differential between when a particular line of the target scene is received by each array 166, 168. With temporally and spatially overlapping matrices of signals for each channel, the signals are then analyzed in the same manner as previously described with respect to a single detector signal, except here there is a much higher degree of resolution of the monitored environment 101. The two matrices of signals are combined to produce a third matrix of signals representing the presence of a particular respiratory component within the monitored environment 101 as previously discussed. The signals may also be imaged by employment of standard imaging techniques.

Figure 15:
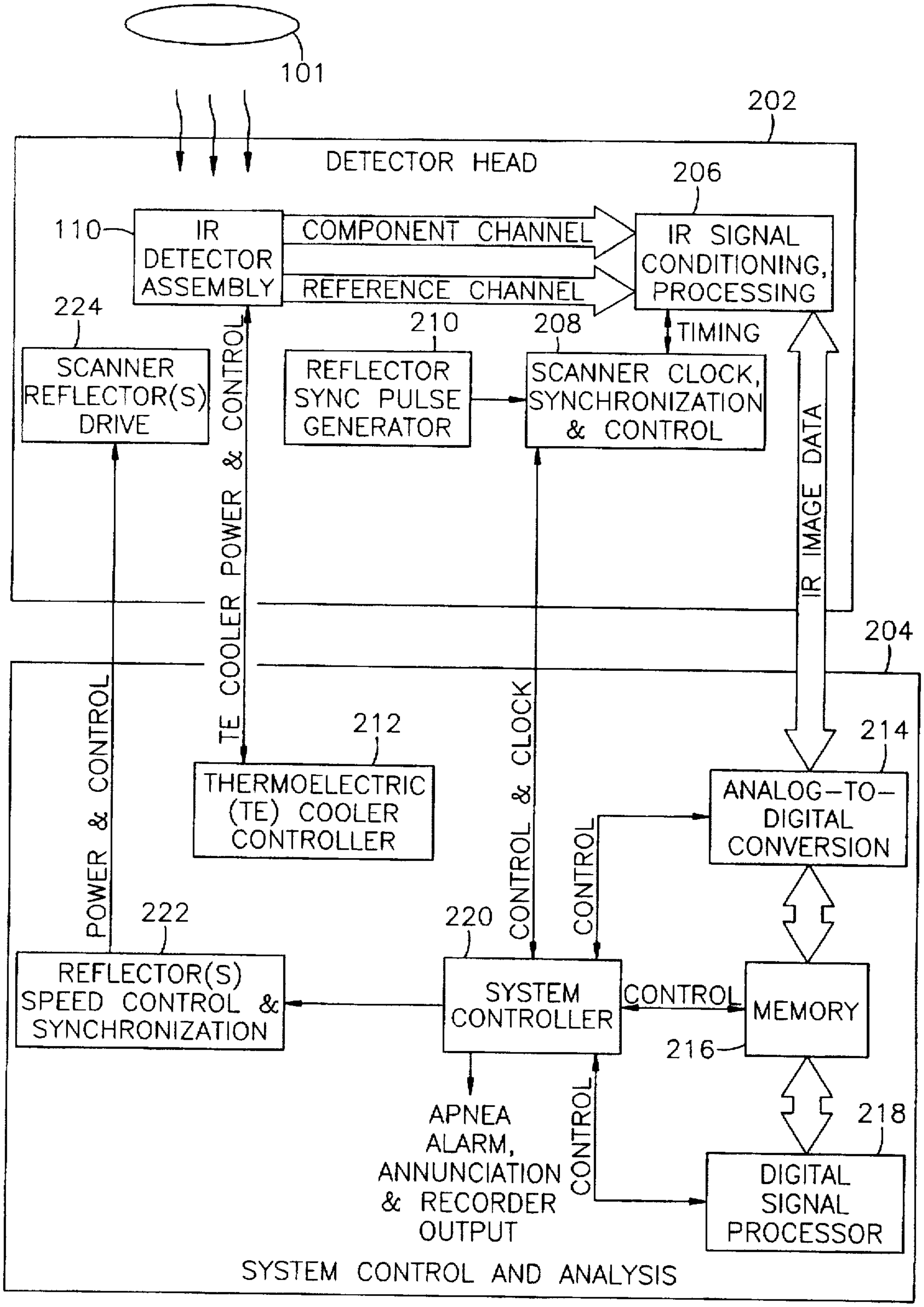
FIG. 15 is a block diagram of an embodiment of the detector assembly and associated processing and control electronics.

FIG. 15 is a block diagram of the detector head 202 and system control and analysis 204 electronics. Component and reference channel data signals are generated by the detector assembly 110 and periodically read by signal conditioning and processing circuitry 206 where the two channels of signals are temporally aligned. Data read and temporal adjustment timing is provided by means of a clock synchronization control circuit 208 which receives an input from reflector synchronization pulse generator 210. Generator 210 is preferably an optical encoder for providing rotational position information to the clock synchronization control 208. As previously discussed, a thermoelectric cooler controller 212 is used to provide solid state cooling of the sensors within the detector assembly 110. Conversion of the sensor signals from analog to digital and processing of the digital signals is similar to that described with reference to FIG. 10B; a significant difference being that there are more signals to process.

To understand the relationship between the arrangement of the sensor arrays 166, 168 and scanning methods, a basic description of imaging techniques might be useful. With reference again to FIG. 13, the region between the imaging optics (lens 108 and reflector 106) and the detector assembly 110 is referred to as image space. The region between the imaging optics and the monitored environment 101 is referred to as object space. A snap-shot image is a picture of the target scene taken essentially instantaneously. The snap-shot image is referred to as a frame. A frame is composed of pixels defined by the intersection of two orthogonal sets of contours, each contour set parallel with one or the other axis of the frame. A pixel represents the smallest resolution element of an image. Pixel size is determined by the number of scan lines or traces the imaging apparatus uses to build an image frame. The greater the number of scan lines, the smaller the pixels for a fixed object or target scene size.

Features of the scene that approach the size of the pixels are not accurately replicated. For example, in an embodiment of the invention that monitors $CO_2$ gas, the smallest area of greater than ambient $CO_2$ gas concentration that must be detected determines the minimum pixel size needed to implement the invention. Therefore, spatial resolution is in direct proportion to the number of pixels in the image. As the number of pixels increases, spatial resolution increases.

With continued reference to the $CO_2$ gas monitoring embodiment, any number of scanning techniques may be used to produce an adequate image for detecting $CO_2$ gas. Relative motion between the detectors and the imaging optics produces the scanning. Scanning mechanisms are located either in object space, image space, or both.

A major advantage of scanning is that it has the same effect upon the D* of the detection system as optical chopping. The frame (matrix of sensor signals) generation rate and the incident IR chopping frequency similarly affect the D*. D* increases in proportion to frame generation rate up to the point at which the detector(s) can no longer keep up with changes in the incident IR profile across the target scene. This is rarely a problem with PbSe detectors. As previously discussed, the typical frequency response of PbSe detectors extends to just under 10 kHz.

Imaging with either a single detector or a detector array having a number of detector elements less than the desired number of pixels along any one dimension of the image requires two-dimensional scanning. For such a detector array, the composite IFOV as represented by the sum of each sensor's IFOV will be scanned. Relative motion along (typically) two orthogonal axes constitutes two-dimensional scanning. A pair of either rotating IR reflectors, oscillating IR reflectors, or a combination of the two is typically used to trace the detector IFOV through a periodic pattern on the object plane such that the area on the object plane defined by the desired total field of view is at least 100% covered. Greater than 100% coverage indicates overlap of parts of the trace pattern. In some cases this is desired for noise reduction, but will further lengthen the time required to build each image frame.

Imaging with a linear detector array such as those illustrated in FIG. 13 with a number of detector elements that is equal to the desired number of pixels along any one dimension of the image requires one-dimensional scanning. Single axis relative motion constitutes one-dimensional scanning. A single rotating or oscillating IR reflector is used to trace the IFOV of all the detectors simultaneously across the area on the object plane defined by the desired total field of view. One major advantage of this system is that the frame generation time of this system is much smaller than the frame generation time associated with the use of a single detector system.

No scanning is required if the system employs a detector array having the same shape as the desired total field of view and has a number of detector elements equal to the desired number of image pixels. Such a system is known as a staring array. The frame rate of the staring system is limited only by the speed of the electronic data acquisition of the detector element outputs. Optical chopping with an IR shuttering device may be used to increase the D* of this system.

It should be noted that the requirement of this invention that the reference and component channel image frames overlap both in space and time is an important factor to consider in selecting a scanning technique. Temporal overlap is required to the extent that the component and reference frames be produced instantaneously compared to the maximum rate at which $CO_2$ gas can be produced and dissipated due to respiration. The spatial overlap requirement affords no such leeway. The component image and the reference image must be of the exact same target scene. The temporal overlap requirement often conflicts with the spatial overlap requirement in trying to arrange the components of the system to accomplish both requirements. Any scanning technique requires some degree of compromise. It is best to use a scheme where the bulk of the compromise lies with the temporal requirement rather than with the spatial overlap requirement.

The present invention may be embodied in other specific forms without departing from its spirit or essential attributes. Accordingly, reference should be made to appended claims rather than the foregoing specification, as indicating the scope of the invention.

What is claimed is:

1. A non-invasive, non-contacting apparatus having imaging optics for determining changes in amounts of a respiratory component present in a predetermined spatial volume intermediate said apparatus and a surface of size determined by the imaged field of view of said optics by detection of infrared energy emitted by said surface or present in said volume and transiting said volume to said apparatus, the apparatus comprising:

first sensor means having a plurality of first sensor elements disposed a distance from said surface substantially equivalent to the object length of said optics for sensing infrared energy emitted by said surface or present in said volume and transiting at least a part of said volume to said first sensor means, for imaging the spatial intensity distribution of infrared energy emitted by said surface or present in said volume and transiting at least a part of said volume to said first sensor means, producing a first image having a plurality of pixels in two-dimensional alignment, wherein at least one of said first sensor elements produces a first signal which indicates the presence or absence of radiation in a first range of wavelengths incident on the elements, said first range of wavelengths including wavelengths to which a respiratory gas of interest is responsive;

second sensor means having a plurality of second sensor elements disposed a distance from said surface substantially equivalent to the object length of said optics for sensing infrared energy emitted by said surface or present in said volume and transiting at least a part of said volume to said second sensor means at substantially the same time as the infrared energy sensed by said first sensor means, for imaging the spatial intensity distribution of infrared energy emitted by said surface or present in said volume and transiting at least a part of said volume to said second sensor means producing a second image having a plurality of pixels in two-dimensional alignment, wherein said second sensor elements produce a second signal which indicates the presence or absence of radiation in a second range of wavelengths incident on the elements which is substantially nonoverlapping with said first range of wavelengths;

wherein said first and second images substantially temporally and spatially overlap; and processing means for processing said first and second images to produce a third image having a plurality of pixels in two-dimensional alignment representing a change in the amount of a respiratory component in said volume, said processing means further comprising means for compensating said first matrix of signals by said second matrix of signals so as to reduce effects on said third matrix of signals of changes in the infrared emissions of said surface or present in said volume.

2. The apparatus as described in claim 1, wherein said respiratory component is $CO_2$ and said first range of wavelengths comprises wavelengths at which $CO_2$ is absorptive.

3. The apparatus as described in claim 1, wherein said respiratory component is $H_2O$ and said first range of wavelengths comprises wavelengths at which $H_2O$ is absorptive.

4. The apparatus as described in claim 1, wherein said respiratory component is a gas selected from the group consisting of a ketone, amino acid, insulin, and pintane, and said first range of wavelengths comprises wavelengths at which said selected gas is absorptive.

5. The apparatus as described in claim 1, further comprising optical means for restricting infrared energy impinging on said first and second sensor elements to infrared energy emitted by said surface or present in said volume.

6. The apparatus as described in claim 5, wherein said optical means comprise an aperture.

7. The apparatus as described in claim 5, wherein said optical means comprise a lens.

8. The apparatus as described in claim 5, wherein said optical means comprise a mirror.

9. The apparatus as described in claim 1, wherein said first or second sensor means comprise a bandpass filter.

10. The apparatus as described in claim 1, wherein said first or second sensor means comprise a bandstop filter.

11. The apparatus as described in claim 1, wherein said processing means comprise means for producing said third image as a function of the difference between said first and second images.

12. The apparatus as described in claim 1, wherein said processing means further comprise means for producing said third image by means of applying non-linear mathematical functions to said first or second images.

13. The apparatus as described in claim 1, wherein said processing means further comprise means for providing said third image by means of an artificial neural network or fuzzy logic system.

14. A passive, non-invasive, non-contacting apparatus for monitoring the respiration of a subject in a monitored environment, the apparatus comprising:

first sensor means for detecting changes in infrared energy signifying and corresponding to changes in concentration in said monitored environment of a respiration component to be monitored, said first sensor means comprising a plurality of first sensor elements, each of said first sensor elements first sensors having an instantaneous field of view comprising at least a portion of the monitored environment, a first optical filter for receiving and filtering said infrared energy to produce first filtered infrared energy comprised of a first range of infrared wavelengths that includes wavelengths of infrared energy absorbed by the respiration component to be monitored, and means for producing a first plurality of signals arranged two-dimensionally from said first sensor elements corresponding to the first filtered infrared energy passed by said first optical filter;

second sensor means for detecting changes in infrared energy signifying reference infrared energy in said monitored environment, said second sensor means comprising a plurality of second sensor elements, each of said second sensor elements having an instantaneous field of view comprising at least a portion of the monitored environment, a second optical filter for receiving and filtering said infrared energy to produce second filtered infrared energy comprised of a second range of infrared wavelengths that includes wavelengths of infrared energy different from wavelengths comprising said first selected range of infrared wavelengths, and means for producing a second plurality of signals arranged two-dimensionally from said second sensor elements corresponding to the second filtered infrared energy passed by said second optical filter;

means for directing infrared energy received from the monitored environment onto said first and second sensor means; and means for processing signals in the first and second pluralities of signals to produce one or more signals corresponding to changes in concentration of said monitored component within the monitored environment.

15. The apparatus as described in claim 14, wherein said means for directing comprises at least one reflector for receiving and reflecting infrared energy from the monitored environment, and at least one optical lens for receiving and directing the reflected infrared energy onto said first and second sensor means.

16. The apparatus as described in claim 15, wherein said at least one reflector comprises at least one moving reflector of infrared energy.

17. The apparatus as described in claim 14, further comprising means for scanning the instantaneous fields of view of said first and second elements to produce the first and second pluralities of signals.

18. The apparatus as described in claim 14, wherein said respiratory component is $CO_2$, and wherein each of said one or more first sensors comprises a lead-selenium element sensitive to infrared energy of wavelengths approximating 3.9 microns, and each of said one or more second sensors comprises a lead-selenium element sensitive to infrared energy of wavelengths approximating 4.28 microns.

19. The apparatus as described in claim 14, further comprising means for imaging said first and second pluralities of signals to produce first and second images of the monitored environment.

20. The apparatus as described in claim 19, wherein said first and second images substantially temporally and spatially overlap.

21. The apparatus as described in claim 14, wherein said first sensor elements comprise a plurality of first sensors arranged into a first one-dimensional matrix of sensors, and said second sensor elements comprise a plurality of second sensors arranged into a second one-dimensional matrix of sensors.

22. The apparatus as described in claim 21, further comprising means for scanning said first and second one-dimensional matrices of sensors to produce the first and second matrices of signals.

23. The apparatus as described in claim 14, wherein said first sensor elements comprise a plurality of first sensor elements arranged into a first two-dimensional matrix of sensors having a first composite field of view of the monitored environment equal to the sum of the instantaneous fields of view of each of the first sensor elements, and said second sensor elements comprise a plurality of second sensor elements arranged into a second two-dimensional matrix of sensors having a second composite field of view of the monitored environment equal to the sum of the instantaneous fields of each of the second sensor elements.

24. The apparatus as described in claim 23, wherein said means for directing is further operable to scan the first and second composite fields of view of said first and second two-dimensional matrices of sensors to produce the first and second pluralities of signals.

25. The apparatus as described in claim 24, wherein said means for directing comprises at least one reflector for receiving and reflecting infrared energy from the monitored environment, and at least one optical lens for receiving and directing the reflected infrared energy onto said first and second sensor means.

26. The apparatus as described in claim 25, wherein said first and second two-dimensional matrices of sensors are positioned to receive reflected infrared energy from each portion of the monitored environment at different times, said apparatus further comprising means for substantially temporally aligning said first and second composite fields of view.

27. The apparatus as described in claim 14, further comprising means for cooling said first and second sensor elements to increase their sensitivity.

28. The apparatus as described in claim 14, further comprising means for chopping said infrared energy to increase the sensitivity of said first and second sensor elements.

29. The apparatus as described in claim 14, wherein said means for processing further comprise means for producing an alarm when a threshold change in the concentration of said monitored component in the monitored environment is detected.

30. A passive, non-invasive, non-contacting apparatus for monitoring the respiration of a subject having a system of organs subserving a respiration function producing $CO_2$ in a monitored environment, said apparatus comprising:

first sensor means in operative communication with said monitored environment, said first sensor means detecting changes in infrared energy signifying and corresponding to changes in the concentration of $CO_2$ in said monitored environment, said first sensor means generating a first plurality of signals arranged two-dimensionally to form a first image;

second sensor means in operative communication with said monitored environment, said second sensor means detecting changes in infrared energy signifying reference infrared energy in said monitored environment, said second sensor means generating a second plurality of signals arranged two-dimensionally to form a second image; and a processing system which converts said first and second images into a third image, said third image signifying the concentration of $CO_2$ in the monitored environment.

31. The apparatus as described in claim 30, wherein said processing system further comprises a filter associated with one of said sensor means which filters from said second signal a component attributable to motion in the monitored environment.

32. The apparatus as described in claim 30, wherein said second sensor means detects changes in infrared energy in a detection range both within and outside the detection range of said first sensor means.

33. The apparatus as described in claim 30, wherein said second sensor means detects changes in infrared energy in a detection range only outside the detection range of said first sensor means.

34. The apparatus as described in claim 30, wherein said first sensor means detects changes in infrared energy in a detection range both within and outside the detection range of said second sensor means.

35. A passive, non-invasive, non-contacting method for monitoring the respiration of a subject having a system of organs subserving a respiration function producing $CO_2$ in a monitored environment, said method comprising the steps of:

detecting changes in signal infrared energy comprising a first range of wavelengths, said changes in signal infrared energy corresponding to changes in the concentration of $CO_2$ in said monitored environment;

generating a first plurality of signals in two-dimensional alignment from detected changes in signal infrared energy;

detecting changes in reference infrared energy comprising a second range of wavelengths which are substantially nonoverlapping with said first range of wavelengths;

generating a second plurality of signals in two-dimensional alignment from detected changes in reference infrared energy;

converting said first and second pluralities of signals into a third plurality of signals in two-dimensional alignment representing the concentration of $CO_2$ present in the monitored environment;

detecting changes in infrared energy in the monitored environment in the absorption wavelength of $H_2O$; and generating a fourth plurality of signals in two-dimensional alignment signifying and corresponding to changes in the concentration in the monitored environment of $H_2O$ vapor.

36. A passive, non-invasive, non-contacting apparatus for monitoring respiration of a subject having a system of organs subserving a respiration function producing $CO_2$ in a monitored environment to provide a concentration of $CO_2$ in the monitored environment, said apparatus comprising:

a first sensor in operative communication with said monitored environment, said first sensor detecting changes in infrared energy which transits said monitored environment, said changes in infrared energy signifying and corresponding to changes in the $CO_2$ concentration in said monitored environment, said first sensor producing a first signal;

a second sensor in operative communication with said monitored environment, said second sensor detecting changes in infrared energy which transits substantially the same monitored environment as infrared energy detected by said first sensor, said changes in infrared energy signifying reference infrared energy in said monitored environment, said second sensor producing a second signal; and a processing system which converts said first and second signals into a third signal, said third signal signifying the concentration of $CO_2$ in the monitored environment.

37. Apparatus in accordance with claim 36, wherein said processing system further comprises a filter associated with one of said sensors which filters from said second signal a component attributable to motion in the detection region.

38. A passive, non-invasive, non-contacting apparatus for monitoring respiration of a subject having a system of organs subserving a respiration function producing $CO_2$ in a monitored environment to provide a concentration of $CO_2$ in the monitored environment, said apparatus comprising:

a first sensor in operative communication with said monitored environment, said first sensor detecting changes in infrared energy signifying and corresponding to changes in the concentration in said monitored environment of a component to be monitored, said first sensor generating a first signal;

wherein said first sensor detects changes in infrared energy in a first detection range within the monitored environment;

a second sensor in operative communication with said monitored environment, said second sensor detecting changes in infrared energy signifying reference infrared energy in said monitored environment, said second sensor generating a second signal, wherein said second sensor detects changes in infrared energy in a second detection range that is both within and outside the first detection range of said first sensor; and a processing system which converts said first and second signals into a third signal, said third signal signifying the concentration of the monitored component in the monitored environment.

39. A passive, non-invasive, non-contacting apparatus for monitoring respiration of a subject having a system of organs subserving a respiration function, said apparatus comprising:

a first sensor in operative communication with said monitored environment, said first sensor detecting changes in infrared energy signifying and corresponding to changes in the concentration in said monitored environment of a component to be monitored, said first sensor generating a first signal;

wherein said first sensor detects changes in infrared energy in a first detection range within the monitored environment;

a second sensor in operative communication with said monitored environment, said second sensor detecting changes in infrared energy within a second detection range signifying reference infrared energy in said monitored environment, said second sensor generating a second signal, wherein said first sensor detects changes in infrared energy in a first detection range that is both within and outside the second detection range of said second sensor; and a processing system which converts said first and second signals into a third signal, said third signal signifying the concentration of the monitored component in the monitored environment.

40. A passive, non-contacting, non-invasive method for monitoring respiration of a subject having a system of organs subserving a respiration function producing $CO_2$ in a monitored environment to provide a concentration of $CO_2$ in the monitored environment, said method comprising the steps of:

detecting changes in infrared energy wherein said changes signify and correspond to changes in the concentration in said monitored environment of $CO_2$;

generating a first signal from said changes in infrared energy of $CO_2$ in the monitored environment;

detecting changes in infrared energy signifying reference infrared energy in said monitored environment;

generating a second signal from said changes in the reference infrared energy;

converting said first and second signals into a third signal signifying the concentration of $CO_2$ in the monitored environment;

detecting changes in infrared energy in the monitored environment in the absorption wavelength of $H_2O$; and generating a fourth signal signifying and corresponding to changes in the concentration in the monitored environment of $H_2O$ vapor.

41. The method of claim 40, further comprising the steps of deriving a ratio of said third and fourth signals signifying and corresponding to changes in blood pH of the subject in the monitored environment.

42. A passive, non-invasive, non-contacting method for monitoring the respiration of a subject having a system of organs subserving a respiration function producing $CO_2$ in a monitored environment, said method comprising the steps of:

detecting changes in signal infrared energy comprising a first range of wavelengths, said changes in signal infrared energy corresponding to changes in the concentration of $CO_2$ in said monitored environment;

generating a first plurality of signals in two-dimensional alignment from detected changes in signal infrared energy;

detecting changes in reference infrared energy comprising a second range of wavelengths which are substantially nonoverlapping with said first range of wavelengths;

generating a second plurality of signals in two-dimensional alignment from detected changes in reference infrared energy; and converting said first and second pluralities of signals into a third plurality of signals in two-dimensional alignment representing the concentration of $CO_2$ present in the monitored environment.

43. A passive, non-invasive, non-contacting method for monitoring the respiration of a subject having a system of organs subserving a respiration function producing a respiratory component in a monitored environment, said method comprising the steps of:

detecting changes in signal infrared energy comprising a first range of wavelengths, said changes in signal infrared energy corresponding to changes in the concentration of a respiratory component in said monitored environment;

generating a first plurality of signals in two-dimensional alignment from detected changes in signal infrared energy;

detecting changes in reference infrared energy comprising a second range of wavelengths which are substantially nonoverlapping with said first range of wavelengths;

generating a second plurality of signals in two-dimensional alignment from detected changes in reference infrared energy; and converting said first and second pluralities of signals into a third plurality of signals in two-dimensional alignment representing the concentration of the respiratory component present in the monitored environment.

* * * * *

UNITED STATES PATENT AND TRADEMARK OFFICE

CERTIFICATE OF CORRECTION

PATENT NO. : 5,800,360

DATED : September 1, 1998

INVENTOR(S) : Roger A. Kisner, Steven P. Baker & R. Bennett Muskin

It is certified that error appears in the above-identified patent and that said Letters Patent is hereby corrected as shown below:

On the title page, in the abstract:

Line 7, "environments" should be --environment--

Line 14, after "$CO_2$" insert--,--

Line 16, after "invention" insert--,--

Signed and Sealed this

Fourth Day of May, 1999

*Attest:*

Q. TODD DICKINSON

*Attesting Officer*

*Acting Commissioner of Patents and Trademarks*

UNITED STATES PATENT AND TRADEMARK OFFICE
CERTIFICATE OF CORRECTION

PATENT NO : 5,800,360
DATED : September 1, 1998
INVENTOR(S) : Roger A. Kisner, Steven P. Baker & R. Bennett Muskin It is certified that error appears in the above-identified patent and that said Letters Patent is hereby corrected as shown below:

Column 1, line 30, after "vapor," insert -- and --.

Column 2, line 10, change "relative" to -- relatively --.

Column 2, line 14, change "the" to -- and --.

Column 2, line 28, after "coverage," insert -- and --.

Column 2, line 29, after "to" insert -- the --.

Column 2, line 47, delete "And", and change "even" to --Even--.

Column 2, line 48, after "process" delete "," and insert -- including --.

UNITED STATES PATENT AND TRADEMARK OFFICE

CERTIFICATE OF CORRECTION

PATENT NO : 5,800,360

DATED : September 1, 1998

INVENTOR(S) : Roger A. Kisner, Steven P. Baker & R. Bennett Muskin

It is certified that error appears in the above-identified patent and that said Letters Patent is hereby corrected as shown below:

Column 2, line 52, after "all" insert -- of which --.

Column 2, line 60, delete "of".

Column 2, line 61, delete "accounting" and insert -- to account --.

Column 2, line 66, after "discloses" insert -- a --.

Column 3, line 8, change "with" to -- will --.

Column 4, line 19, after "Thus", insert -- , --.

Column 4, line 25, change "spectrum" to -- spectra --.

UNITED STATES PATENT AND TRADEMARK OFFICE

CERTIFICATE OF CORRECTION

PATENT NO : 5,800,360

DATED : September 1, 1998

INVENTOR(S) : Roger A. Kisner, Steven P. Baker & R. Bennett Muskin

It is certified that error appears in the above-identified patent and that said Letters Patent is hereby corrected as shown below:

Column 4, line 40, delete "spectrum; and" and insert -- spectrum. --.

Column 4, line 51, delete "the presence of".

Column 4, line 52, after "sources" delete -- from --.

Column 4, line 53, after "etc.)" insert -- is present --.

Column 4, line 53, after "environment," insert -- and further because --.

Column 4, line 55, after "of", insert -- detectable --.

Column 4, line 61, after "from", insert -- sources --.

Column 5, line 29, after "for", insert -- an --.

UNITED STATES PATENT AND TRADEMARK OFFICE

CERTIFICATE OF CORRECTION

PATENT NO : 5,800,360

DATED : September 1, 1998

INVENTOR(S) : Roger A. Kisner, Steven P. Baker & R. Bennett Muskin

It is certified that error appears in the above-identified patent and that said Letters Patent is hereby corrected as shown below:

Column 5, line 63, after "monitoring", delete "the".

Column 6, line 28, after "produce", insert -- any --.

Column 8, line 51, after "example", insert -- , --.

Column 9, line 40, after "charge", insert -- , --.

Column 10, line 24, after "observed", delete "as".

Column 11, line 19, change "last" to -- far right --.

Column 12, line 21, delete "," after "independent".

UNITED STATES PATENT AND TRADEMARK OFFICE

CERTIFICATE OF CORRECTION

PATENT NO : 5,800,360

DATED : September 1, 1998

INVENTOR(S) : Roger A. Kisner, Steven P. Baker & R. Bennett Muskin

It is certified that error appears in the above-identified patent and that said Letters Patent is hereby corrected as shown below:

Column 12, line 65, after "25", insert -- , --.

Column 13, line 9, after "change", insert -- in --.

Column 13, line 10, change "of" to -- for --.

Column 13, line 12, after "4", delete ",".

Column 13, line 28, change "of" to -- for --.

Column 13, line 54, change "an" to -- a --.

Column 14, line 59, change "11D" to -- 11 --.

UNITED STATES PATENT AND TRADEMARK OFFICE
CERTIFICATE OF CORRECTION

PATENT NO : 5,800,360
DATED : September 1, 1998
INVENTOR(S) : Roger A. Kisner, Steven P. Baker & R. Bennett Muskin It is certified that error appears in the above-identified patent and that said Letters Patent is hereby corrected as shown below:

Column 15, line 26, change "fuzz-logic" to --fuzzy logic--

Column 15, line 33, after "comprises" insert -- a --.

Column 16, line 8 , change "fuzzy-logic" to --fuzzy logic--

Column 18, line 60, delete "$CO_2$-Motion" and insert -- $CO_2$ motion --.

Column 22, line 12, after "array" insert -- , --.

Column 22, line 13, after "13", insert -- , --.

Signed and Sealed this

Fourth Day of May, 1999

Attest:

Q. TODD DICKINSON

*Attesting Officer* — *Acting Commissioner of Patents and Trademarks*